(12) United States Patent
Lemanski et al.

(10) Patent No.: US 7,271,254 B2
(45) Date of Patent: Sep. 18, 2007

(54) PROMOTING CARDIAC CELL DIFFERENTIATION

(75) Inventors: Larry F. Lemanski, Boynton Beach, FL (US); Chi Zhang, Pompano Beach, FL (US)

(73) Assignee: Florid Atlantic University, Boca Raton, FL (US)

( * ) Notice: Subject to any disclaimer, the term of this patent is extended or adjusted under 35 U.S.C. 154(b) by 0 days.

(21) Appl. No.: 10/822,496

(22) Filed: Apr. 12, 2004

(65) Prior Publication Data

US 2004/0203044 A1    Oct. 14, 2004

Related U.S. Application Data

(60) Provisional application No. 60/462,171, filed on Apr. 10, 2003.

(51) Int. Cl.
*C07H 21/02* (2006.01)
*C07H 21/04* (2006.01)
*C12Q 1/68* (2006.01)
*C12N 15/00* (2006.01)

(52) U.S. Cl. .................. 536/23.1; 435/6; 435/69.1; 435/320.1

(58) Field of Classification Search .................. 514/12; 435/6, 69.1; 536/23.1; 436/320.1
See application file for complete search history.

(56) References Cited

OTHER PUBLICATIONS

Lemanski, L.F., et al. A Specific Synthetic RNA Promotes Cardiac Myofibrillogenesis in the Mexican Axolotl. (1996) Biochem. Biophys. Res. Comm. 229(3): 974-981.*

Davis et al., "Induction of myofibrillogenesis in cardiac lethal mutant axolotl hearts rescued by RNA derived from normal endoderm," Development 99:145-154, 1987.

Draghia-Akli, "Enhanced growth by ectopic expression of growth hormone releasing hormone using an injectable myogenic vector," Nat Biotechnol. 15:1285-9, 1997.

Fransen et al., "Myocardial cell relationships during morphogenesis in normal and cardiac lethal mutant axolotls, Ambystoma mexicanum," Amer J Anat 183:245-257, 1998.

Lemanski, L. "Role of Tropomyosin in Actin Filament Formation in Embryonic Salamander Heart Cells," J Cell Biol 82:227-238, 1979.

Lemanski et al., "Normal Anterior Endoderm Corrects the Heart Defect in Cardiac Mutant Salamanders (Ambystoma mexicanum)," Science 204:860-862, 1979.

Lemanski et al., The Cardiac Mutant Gene c in Axolotls: Cellular, Developmental and Molecular Studies, Cell Molec Biol Res 41: 293-305, 1995.

Lemanski et al., Molecular biology of heart development in the Mexican axolotl, Ambystoma mexicanum, J Tsitologiya (Cytology) 39:918-927, 1997.

Lemanski et al., "Cellular, Molecular, and Developmental Studies on Heart Development in Normal and Cardiac Mutant Axolotls, Ambystoma Mexicanum," Chapter 12.

(Continued)

*Primary Examiner*—Maryam Monshipouri
*Assistant Examiner*—Marsha Tsay
(74) *Attorney, Agent, or Firm*—Akerman Senterfitt; Nicholas A. Zachariades

(57) ABSTRACT

Compositions and methods for inducing a cardiac muscle phenotype, such as rhythmic contraction and formation of myofibrils, in a cell are described. Disclosed are nucleic acids encoding myofibrillogenesis-inducing RNA (MIR) molecules, RNA molecules (MIR) and RNA-binding proteins that bind to MIR to induce myofibrillogenesis and vectors comprising these nucleic acids. Also included is a method of promoting cardiac muscle differentiation using these compositions.

5 Claims, 8 Drawing Sheets

OTHER PUBLICATIONS

Smith et al., "Heart induction in wild-type and cardiac mutant axolotls (Amybstoma mexicanum)," J Exp Zool 254:48-54, 1990.

Lemanski et al., "A specific synthetic RNA promotes cardiac myofibrillogeneses in the Mexican axolotol," Biochem Biophys Res Commun 229:974-81, 1996.

Lemanski et al., "Creation of chimeric mutant axolotls: a model to study early embryonic heart development in Mexican axolotls," Anat Embryol 203:335-342, 2001.

Pestova et al. "Molecular mechanisms of translation initiation in eukaryotes," Proc Natl Acad Sci 98:7029-7036, 2001.

Sanbe et al., "Reengineering inducible cardiac-specific transgenesis with an attenuated myosin heavy chain promoter," Circ Res. 92:609-16, 2003.

Sepulveda et al., "Combinatorial expression of GATA4, Nkx2-5, and serum response factor directs early cardiac gene activity," J Biol Chem. 277:25775-82, 2002.

Zackson et al., "Cranial neural crest cells exhibit directed migration on the pronephric duct pathway: further evidence for an in vivo adhesion gradient," Dev Biol 117:342-353, 1986.

Zajdel et al., "Alteration of cardiac myofibrillogenesis by lioposme-mediated delivery of exogenous proteins and nucleic acids into whole embryonic hearts," Anat Embryol 201:217-228, 1999.

Zhang et al., Cloning of a Myofibril Inducing RNA (MIR) that Promotes Myofibrillogenesis, FASEB J., Apr. 2004, vol. 18, No. 4-5, pp. Abst. 4942.

Chen et al., Genetics of heart Development, Trends in Genetics, Sep. 2000, vol. 16, No. 9, pp. 383-388.

Hatcher et al., Atrail Form and Function: Lessons from Human Molecular Genetics, Trends in Cardiovascular Medicine, 2000, vol. 10, No. 3, pp. 93-101.

* cited by examiner

```
Normal:   1  agcaccactccatttttggaacacctcctctaccgtggatgagaggcggagccgatcctt   60
             ||||||||||||||||||||||||||||||||||||||||||||||||||||||||||||
Mutant:   1  agcaccactccatttttggaacacctcctctaccgtggatgagaggcggagccgatcctt   60

Normal:  61  tggaatttgtacatgtgacctcaaggttgcacgcatatccgagcagttgctggattagag  120
             |||||||||||||||||||||||||||||||||||*||||||||||||||||||||||||
Mutant:  61  tggaatttgtacatgtgacctcaaggttgcactcatatccgagcagttgctggattagag  120

Normal: 121  caggcactcccttatcggctttggaatggagaccagaaagaacact   166
             ||||||||||||||||||||||||||||||||||||||||||||||
Mutant: 121  caggcactcccttatcggctttggaatggagaccagaaagaacact   166
```

FIG. 3

No.1→ GTTCAAAAATAACATTTTAAT
TTTGTATCTCCTAATACAGCCATCATAACATATTCTAGGACTGGTATAAC
TGTATAGACAAACTCCCTTCCTAGGATATTTTGGGAAAGTGCTGGATAGC
CGGGGAGAACAGCACCTTTCTCTCAGGCAATGTTAAATAGGTGCAATGTT
TTCACATGTTATGGAATATATCTTCCAACTGACTGACCAAGAGAAAACAA
TGAACCACAATACCGGAAACTTCATTCGTTTGACCCTTCCACCCACTCGA
GCGTCAACATGCCCAGGCCGCTACCCCTTGACACACGTGTAGCACCACTC
CATTTTTGGAACACCTCCTCTACCGTGGATGAGAGGCGGAGCCGATCCTT
*TGGAATTTGTACATGTGACCTCAAGGTTGCACGCATATCCGAGCAGTTGC*
*TGGATTAGAGCAGGCACTCCCTTATCGGCTTTGGAATGGAGACCAGAAAG*
*AACAATGTGGACAGCTGATATGGAGGGCAGGGCGGGGAAGTGAGAGAAA*
    * (+Poly A)
GGGCAACAATAGAGGGCAGATAAAGGGGGGACGGCAAGGAATAAACAGGA
ACTGCAGTGGGAGAAAACGTCGAACGAGAAAAAAAAAAAAAAAAAAAAA←
No.620

AxoSmN Full-length cDNA Sequence

```
AGCCGATCCTTTGGAATTTGTACATGTGACCTCAAGGTTGCACGCATATC
CGAGCAGTTGCTGGATTAGAGCAGGCACTCCCTTGCTCCAACACGTTGAC    100
TTTAGGATGCGCTGTATCCTGCAAGATGGCCGCATCTTTATTGGTACTTT
CAAAGCTTTCGATAAACACATGAATCTGATTCTCTGTGACTGCGACGAGT    200
TCAGGAAGATAAAACCTAAGAATTCTAAACAGCCAGAGCGTGAAGAGAAG
AGGGTCCTTGGGCTGGTACTACTCCGTGGCGAAAACGTTGTATCTATGAC    300
CGTGGAAGGACCACCCCCAAAAGATACTGGTATTGCCCGTGTCCCACTGG
CAGGAGCTGCAGGAGGACCTGGTGTTGGAAGGGCTGCAGGGAGAGGAGTG    400
CCAGCAGGTGTACCAATACCGCAAGCACCAGCGGGCTTGGCAGGCCCAGT
GCGAGGTGTTGGTGGCCCATCCCAGCAGGTGATGACACCACAGGGACGTG    500
GAAATCCATCTGGTGCTAGCATTGCAGGAGCACCAACGCAGTACCAGCCT
GGTGGGAGAGGTGGCCCGATGCTGCCAATGGGCTGTGGTGGACCTCCAGG    600
CATGATGGGACCACCCCCGGGCATGAGGCCACCTATGGGCCCACCTATGG
GAATGCCCCCAGGCCGAGGTGGTTCAATGGGCATGCCTCCACCTGGTATG    700
CGACCTCCACCACCTGGTATGAGAGGCGACCGATTCTAGAAACAAAGGTT
CACCTCGTGGGAAGCGTTCCTCAAGACCATAAATCGATTACTTGTTTGTG    800
GATTGAAAGTTGATGGATGTGTTGAGTGGATCCCAGTGCACTTACTGGC
AGTTGGAAGCCCTTGATAGTAGCTACTTTTACTTTCAGGAGATCTGGCTG    900
AAGCTGTTCATTTTTCTTATTTACATGTAAATGTTTTTAATAAACTTCTA
AAATGGCAAAAAAAAAAAAAAAAAAAAAAAAAAAA
```

B

AxoSmN Amino Acid Sequence:

MRCILQDGRIFIGTFKAFDKHMNLILCDCDEFRKIKPKNSKQPEREEKRVLGLVLLRGE
NLVSMTVEGPPPKDTGIARVPLAGAAGGPGVGRAAGRGVPAGVPIPQAPAGLAGPVRGV
GGPSQQVMTPQGRGNPSGASIAGAPTQYQPGGRGGPMLPMGCGGPPGMMGPPPGMRPPM
GPPMGMPPGRGGSMGMPPPGMRPPPPGMRGDRF

FIG. 8

PROMOTING CARDIAC CELL DIFFERENTIATION

CROSS-REFERENCE TO RELATED APPLICATIONS

The present application claims the priority of U.S. provisional patent application No. 60/462,171 entitled "Promoting Cardiac Cell Differentiation," filed on Apr. 10, 2003. The foregoing is incorporated herein by reference in its entirety.

STATEMENT REGARDING FEDERALLY SPONSORED RESEARCH

This invention was made with U.S. government support under grant numbers RO1 HL061246, 2RO1 HL061246-06A1, and R01 HL58435, awarded by the National Institutes of Health. The U.S. government may have certain rights in the invention.

FIELD OF THE INVENTION

This invention relates generally to the fields of molecular biology and medicine. More particularly, the invention relates to methods of inducing and restoring cardiac muscle function.

BACKGROUND

Establishment and maintenance of normal heart cell function is essential to the survival of all higher organisms. During normal development, cells destined to become cardiac muscle cells undergo a process of differentiation whereby they form highly organized myofibrils capable of constant, rhythmic contraction. Myofibrillogenesis refers to the process whereby these fibrils are formed. In disease conditions affecting heart muscle, such as heart attack, stroke and congenital abnormalities, healthy heart cells fail to develop or are lost. Understanding of the mechanisms underlying control of myofibrillogenesis and cardiac muscle cell differentiation holds promise for restoring damaged heart muscle.

Previous studies have identified a cardiac mutant in a salamander, the Mexican axolotl with a defect in myofibrillogenesis. In this model, a cardiac lethal gene c is expressed in homozygous recessive animals. Matings between heterozygous parents (+/c×+/c) provide 25% mutant embryos (c/c) which are first distinguishable from their normal siblings (+/+ or +/c) at stage 34, when normal embryos develop contracting hearts. Mutant embryos form hearts that fail to beat and subsequently die from lack of circulation. The normal siblings mature to adulthood, exhibiting no obvious abnormalities (Humphrey, 1968).

Embryonic heart development in this species proceeds by a two-step mechanism (Smith and Armstrong, 1990). The first step, occurring during neurulation, is endoderm-dependent and directs early cardiac morphogenesis. This step is apparently normal in cardiac mutant hearts, which undergo early morphogenesis that is indistinguishable from that of normal hearts (Lemanski, 1973; Fransen and Lemanski, 1988). The second step involves myofibrillogenesis and the completion of differentiation into muscle tissue. In the mutant animals, the hearts become distended and thin-walled after heartbeat stage 35. The embryos subsequently develop ascites and survive only to stage 41, about 20 days after the normal time of onset of heart beating. However, mutant embryos swim normally, indicating that gene c does not affect skeletal muscle.

As the elderly population increases, and as larger segments of the population are subjected to high-stress employment situations, cardiovascular disease is becoming increasingly prevalent. The need for development of new therapeutic methods for restoring heart muscle cells continues to rise. Promising technologies of the future, such as replacement of damaged heart cells with cardiac cells grown in culture, are dependent upon finding the molecular keys to inducing a cardiac muscle cell phenotype.

SUMMARY

The invention pertains to compositions and methods for inducing a cardiac muscle phenotype in a cell. More specifically, it relates to the use of myofibrillogenesis-inducing RNA (MIR) to induce muscle cell differentiation in a cell.

The invention provides in one aspect a purified nucleic acid including a nucleotide sequence that encodes a myofibrillogeneis-inducing RNA (MIR) molecule having at least one functional activity of a native MIR molecule.

The nucleotide (DNA) sequence of the purified nucleic acid can encode an RNA molecule having a secondary structure that permits specific binding to at least one MIR-binding protein.

The nucleotide (DNA) sequence can be a sequence whose complement hybridizes under stringent hybridization conditions to the nucleotide sequence of at least one of SEQ ID NO:2 and SEQ ID NO:3.

The nucleotide sequence can include SEQ ID NO:1 and can be greater than 166 nucleotides in length. The nucleotide sequence can share at least 75% sequence identity with SEQ ID NO:5. The nucleotide sequence can include SEQ ID NO:5.

A portion of the purified nucleotide sequence that encodes a MIR molecule can include a first polynucleotide sequence that shares sequence identity with a second polynucleotide sequence within the 5' untranslated region of a second nucleic acid that encodes an RNA splicing factor. In some embodiments, the RNA splicing factor is SmN. The first and second identical polynucleotide sequences can include the sequence of SEQ ID NO:6

Also within the invention are purified ribonucleic acid (RNA) molecules. Accordingly, the invention further includes a purified myofibrillogenesis-inducing RNA (MIR) molecule including an RNA sequence is a complement of a DNA sequence that encodes a myofibrillogeneis-inducing RNA (MIR) molecule having at least one functional activity of a native MIR molecule. In some embodiments, the deoxyribonucleotide (DNA) sequence encodes an RNA molecule that is between about 167 and about 620 nucleotides in length. The DNA sequence encoding the MIR can include the sequence of SEQ ID NO:1. The DNA sequence can include SEQ ID NO:5.

Some embodiments of the nucleic acids of the invention are used for gene therapy. Accordingly, in another aspect the invention includes vectors including a purified nucleic acid that encodes a myofibrillogeneis-inducing RNA (MIR) molecule having at least one functional activity of a native MIR molecule. Some versions of the vectors further include a purified nucleic acid that encodes a MIR-binding protein.

Yet a further aspect of the invention is a method of inducing a cardiac muscle phenotype in a cell. The method includes the steps of: (a) providing a cell including at least one MIR-binding protein; and (b) contacting the cell with at least one MIR molecule that specifically binds to the at least one MIR-binding protein, in an amount sufficient to induce a cardiac muscle phenotype in the cell. The cardiac muscle phenotype in the cell can include formation of myofibrils or rhythmic contraction of the cell. In some embodiments, the MIR-binding proteins can have molecular weights in the range of about 11-13 kDa and about 28-30 kDa.

In some versions of the method, the MIR molecule can be encoded by a nucleic acid including a sequence that is less than 166 nucleotides in length which shares at least 75% sequence identity with SEQ ID NO:1. In other versions, the sequence can be at least 167 nucleotides in length and share at least 75% sequence identity with SEQ ID NO:5.

In the practice of the method, the MIR-binding protein can be exogenously added to the cell.

In some embodiments of the method, step (b) includes contacting the cell with a vector that includes a nucleic acid that encodes at least one MIR molecule. The nucleic acid in the vector can further include a nucleotide sequence that encodes a MIR-binding protein.

The cell used in the method of inducing a cardiac muscle phenotype can be a stem cell, for example one grown in tissue culture. In other variations of the method, the cell can be situated within a heart, for example in an area of damaged heart muscle in a living subject.

As used herein, "bind," "binds," or "interacts with" means that one molecule recognizes and adheres to a particular second molecule in a sample, but does not substantially recognize or adhere to other structurally unrelated molecules in the sample. Generally, a first molecule that "specifically binds" a second molecule has a binding affinity greater than about $10^5$ to $10^6$ moles/liter for that second molecule.

"Gene therapy," as used herein refers to the treatment of inherited or acquired diseases by the introduction and expression of genetic information in cells.

As used herein, a "nucleic acid" or a "nucleic acid molecule" means a chain of two or more nucleotides such as ribonucleic acid (RNA) and deoxyribonucleic acid (DNA). A "purified" nucleic acid molecule is one that has been substantially separated or isolated away from other nucleic acid sequences in a cell or organism in which the nucleic acid naturally occurs (for example, 30, 40, 50, 60, 70, 80, 90, 95, 96, 97, 98, 99, 100% free of contaminants). The term includes, for example, a recombinant nucleic acid molecule incorporated into a vector, a plasmid, a virus, or a genome of a prokaryote or eukaryote. Examples of purified nucleic acids include cDNAs, fragments of genomic nucleic acids, nucleic acids produced by polymerase chain reaction (PCR), nucleic acids formed by restriction enzyme treatment of genomic nucleic acids, recombinant nucleic acids, and chemically synthesized nucleic acid molecules. A "recombinant" nucleic acid molecule is one made by an artificial combination of two otherwise separated segments of sequence, for example, by chemical synthesis or by the manipulation of isolated segments of nucleic acids by genetic engineering techniques.

As used herein, the term "MIR," (for "myofibrillogenesis-inducing RNA") refers to a nucleic acid in the form of an RNA molecule. The term "MIR" may also be used synonymously with the term "MIR RNA." Nucleic acids, i.e., DNA molecules that encode and may be complementary to MIR polyribonucleotide sequences are referred to herein as "MIR-encoding" nucleic acids, "MIR-encoding" nucleotides, polynucleotides, deoxyribonucleotides and the like, or "MIR cDNA."

When referring to hybridization of one nucleic acid to another, "low stringency conditions" means in 10% formamide, 5× Denhardt's solution, 6×SSPE, 0.2% SDS at 42° C., followed by washing in 1×SSPE, 0.2% SDS, at 50° C.; "moderate stringency conditions" means in 50% formamide, 5× Denhardt's solution, 5×SSPE, 0.2% SDS at 42° C., followed by washing in 0.2×SSPE, 0.2% SDS, at 65° C.; and "high stringency conditions" means in 50% formamide, 5× Denhart's solution, 5×SSPE, 0.2% SDS at 42° C., followed by washing in 0.1×SSPE, and 0.1% SDS at 65° C. The phrase "under stringent conditions" means under low, moderate, or high stringency conditions.

As used herein, the term "vector" refers to a nucleic acid molecule capable of transporting another nucleic acid to which it has been linked. One type of vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors."

A first nucleic acid sequence is "operably" linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked nucleic acid sequences are contiguous and, where necessary to join two protein coding regions, in reading frame.

A cell, tissue, or organism into which has been introduced a foreign nucleic acid, such as a recombinant vector, is considered "transformed," "transfected," or "transgenic." A "transgenic" or "transformed" cell also includes progeny of the cell.

Unless otherwise defined, all technical terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference for the proposition cited. In the case of conflict, the present specification, including any definitions will control. In addition, the particular embodiments discussed below are illustrative only and not intended to be limiting.

Other features and advantages of the invention will be apparent from the following detailed description, and from the claims.

BRIEF DESCRIPTION OF THE DRAWINGS

This invention may be better understood by referring to the following description taken in conjunction with the accompanying drawings, in which:

FIG. 3. shows alignment of DNA sequences encoding normal (SEQ ID NO: 1) and mutant (SEQ ID NO: 4) MIR RNA sequences. The indicated 166 bp MIR nucleotide sequence from normal embryos is capable of "rescuing" heart function in mutant embryos. Comparison of nucleotide sequences in normal and cardiac mutant (c/c) embryos reveals a G to T point mutation at position 93 (G93T, *) within the mutant sequence.

FIG. 7 shows a DNA sequence encoding a full-length expressed sequence of MIR, identified herein as SEQ ID NO:5. Arrows indicate nucleotides at position numbers 1 and 620.

FIG. 8A shows a full-length cDNA sequence of axoSmN (SEQ ID NO.: 7) from the Mexican axolotl. The underlined sequence within the 5' untranslated region is a 100% match with a portion of the MIR cDNA encoding bioactive MIR. FIG. 8B shows an amino acid sequence for axoSnN (SEQ ID NO.: 8).

DETAILED DESCRIPTION

Figure 1:
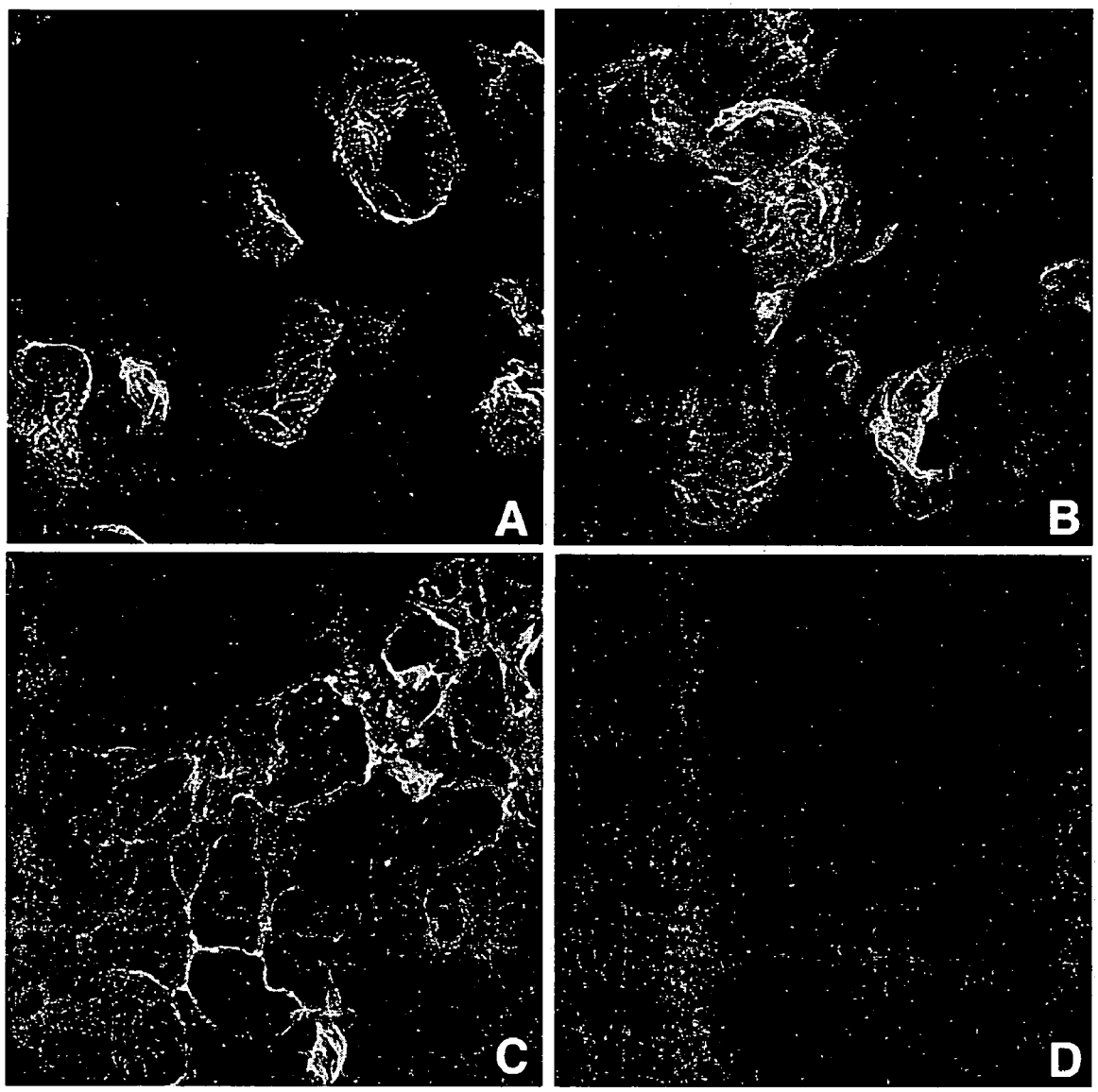
FIG. 1 shows confocal micrographs of organ-cultured hearts following immunostaining with anti-tropomyosin antibody. (A) normal heart; (B) mutant heart cultured with positive control RNA from embryonic endoderm; (C) mutant heart cultured with adult sheep heart RNA; (D) mutant heart cultured with RNase-treated sheep heart RNA. Tropomyosin staining is apparent in (A)-(C), but absent in (D).

Myofibrillogenesis inducing RNA (MIR) is an RNA molecule expressed in embryonic endoderm, with the ability to induce formation of myofibrils in differentiating cardiomyocytes of normal, but not mutant individuals, in an animal model of heart development.

In studies disclosed herein, the full-length nucleotide sequence of MIR is disclosed. It is further shown that MIR extracted from adult mammalian (sheep) heart has the ability to promote ("rescue") heart cell differentiation in mutant salamanders, enabling these cells to exhibit normal rhythmic contractions, tropomyosin distribution, and myofibril formation. Detection of RNA-protein interactions by Northwestern blotting and gel-shift assays further led to the isolation of two MIR-binding proteins having molecular weights (MW) of about 13-15 kDa and about 28-30 kDa. Comparison of MIR DNA sequences from normal and mutant embryos revealed a point mutation in the mutant DNA that resulted in the loss of functional (rescue) ability of the RNA, coupled with inability to bind the larger MW MIR-binding protein. Taken together, these results demonstrate that myofibrillogenesis and promotion of a normal cardiac muscle phentotype can be achieved through the interaction of MIR RNA with one or more MIR-binding proteins. The below described preferred embodiments illustrate adaptations of these compositions and methods. Nonetheless, from the description of these embodiments, other aspects of the invention can be made and/or practiced based on the description provided below.

Biological Methods

Methods involving conventional molecular biology techniques are described herein. Such techniques are generally known in the art and are described in detail in methodology treatises such as Molecular Cloning: A Laboratory Manual, 2nd ed., vol. 1-3, ed. Sambrook et al., Cold Spring Harbor Laboratory Press, Cold Spring Harbor, N.Y., 1989; and Current Protocols in Molecular Biology, Ausubel et al. eds., Greene Publishing and Wiley-Interscience, New York, 1992 (with periodic updates). Various techniques using polymerase chain reaction (PCR) are described, for example, in Innis et al., PCR Protocols: A Guide to Methods and Applications, Academic Press: San Diego, 1990. PCR primer pairs can be derived from known sequences by known techniques, such as use of computer programs intended for that purpose (for example, Primer, Version 0.5, 1991, Whitehead Institute for Biomedical Research, Cambridge, Mass.). Methods for chemical synthesis of nucleic acids are discussed, for example, in Beaucage and Carruthers, Tetra Letts 22:1859-1862, 1981, and Matteucci et al., J Am Chem Soc 103:3185, 1981. Chemical synthesis of nucleic acids can be performed, for example, on commercial automated oligonucleotide synthesizers.

Immunological methods (for example, preparation of antigen-specific antibodies, immunoprecipitation, and immunoblotting and immunolocalization) are described, for example, in Current Protocols in Immunology, Coligan et al., eds., John Wiley & Sons, New York, 1991; and Methods of Immunological Analysis, Masseyeff et al., eds., John Wiley & Sons, New York, 1992.

Conventional methods of gene transfer and gene therapy can also be adapted for use in the present invention. See, for example, Gene Therapy: Principles and Applications, T Blackenstein, ed., Springer Verlag, 1999; Gene Therapy Protocols (Methods in Molecular Medicine), P D Robbins ed., Humana Press, 1997; and Retro-vectors for Human Gene Therapy, C P Hodgson, ed., Springer Verlag, 1996.

Myofibrillogenesis-Inducing RNA (MIR) Nucleic Acids

The invention provides in one aspect a purified nucleic acid comprising a nucleotide sequence that encodes a myofibrillogenesis-inducing RNA (MIR) molecule having at least one functional activity of a native MIR molecule. The nucleic acid can be a deoxyribonucleic acid (DNA) that encodes an RNA molecule having a secondary structure that permits specific binding to at least one MIR-binding protein.

MIR-encoding DNA molecules utilized in the present invention may be in the form of cDNA, genomic DNA, or synthetic DNA. The DNA may be double-stranded or single-stranded, and if single-stranded, may be the coding (sense) strand or non-coding (anti-sense) strand.

In another aspect, the invention includes nucleic acids in the form of myofibrillogenesis-inducing ribonucleic acid (RNA) molecules (MIR) that are encoded by the DNA molecules of the invention and by definition are complementary to the DNA molecules. The RNA molecules of the invention are shown herein to have bioactive properties such as 1) inducing heart beating and myofibrillogenesis in the muscle cells of embryonic hearts and 2) binding to specific MIR-binding proteins. The latter interaction is thought to promote transcription of genes, such as tropomysosin, associated with muscle cell differentiation. Additionally, it is shown herein that a fragment of a MIR-encoding cDNA (i.e., SEQ ID NO:6) shares 100% identity with a sequence in the 5' untranslated region of the axolotl homolog of SmN, an RNA splicing factor (Huntriss J D et al., 1993. Nucleic Acids Res. August 25;21(17):4047-53), further supporting a role for MIR in regulation of muscle cell differentiation. In preferred embodiments, the MIR molecules of the invention are between about 167 and about 620 nucleotides in length.

MIR-encoding (i.e., DNA) nucleic acid molecules of the invention can include the DNA sequence encoding the polyribonucleotide sequence of any MIR molecule known to induce a cardiac muscle phenotype in a cell. Methods for amplification of full-length and partial coding sequences of MIR RNA, for example by RT-PCR using specific primers, and genomic walking using techniques such as 3'- and 5'-RACE are known to those of skill in the art of molecular biology, and are further described in examples below. For instance, primers having the nucleic acid sequences of SEQ ID NOs:2 and 3 can first be utilized to amplify a 166 nucleotide bioactive MIR-encoding partial cDNA sequence from axolotl tissues. Other primers may be designed based on the sequences of one or both of these primers to obtain MIR-encoding molecules of different lengths. As but one example, nucleic acids of the invention can include nucleotide sequences whose complement hybridizes under stringent conditions to the nucleotide sequence of at least one MIR-specific primer, such as SEQ ID NO:2 or SEQ ID NO:3.

The coding sequence which encodes a native MIR-encoding nucleic acid may be identical to SEQ ID NO:5, which is derived from axolotl. It may also be a different coding sequence which, as a result of the redundancy or degeneracy of the genetic code, encodes the same RNA. Other nucleic acid molecules within the invention are variants of a native MIR-encoding nucleic acid, such as those that encode fragments, analogs and derivatives of a native MIR. Variants may be, for example, a naturally occurring allelic variant of a native MIR nucleic acid, a homolog of a native MIR nucleic acid, or a non-naturally occurring variant of a native MIR nucleic acid. These variants can have a nucleotide sequence that differs from a native MIR nucleic acid sequence in one or more bases. For example, the nucleotide sequence of such variants can feature a deletion, addition, or substitution of one or more nucleotides of a native MIR nucleic acid. Nucleic acid insertions are preferably of about 1 to 10 contiguous nucleotides, and deletions are preferably of about 1 to 30 contiguous nucleotides.

Figure 5:
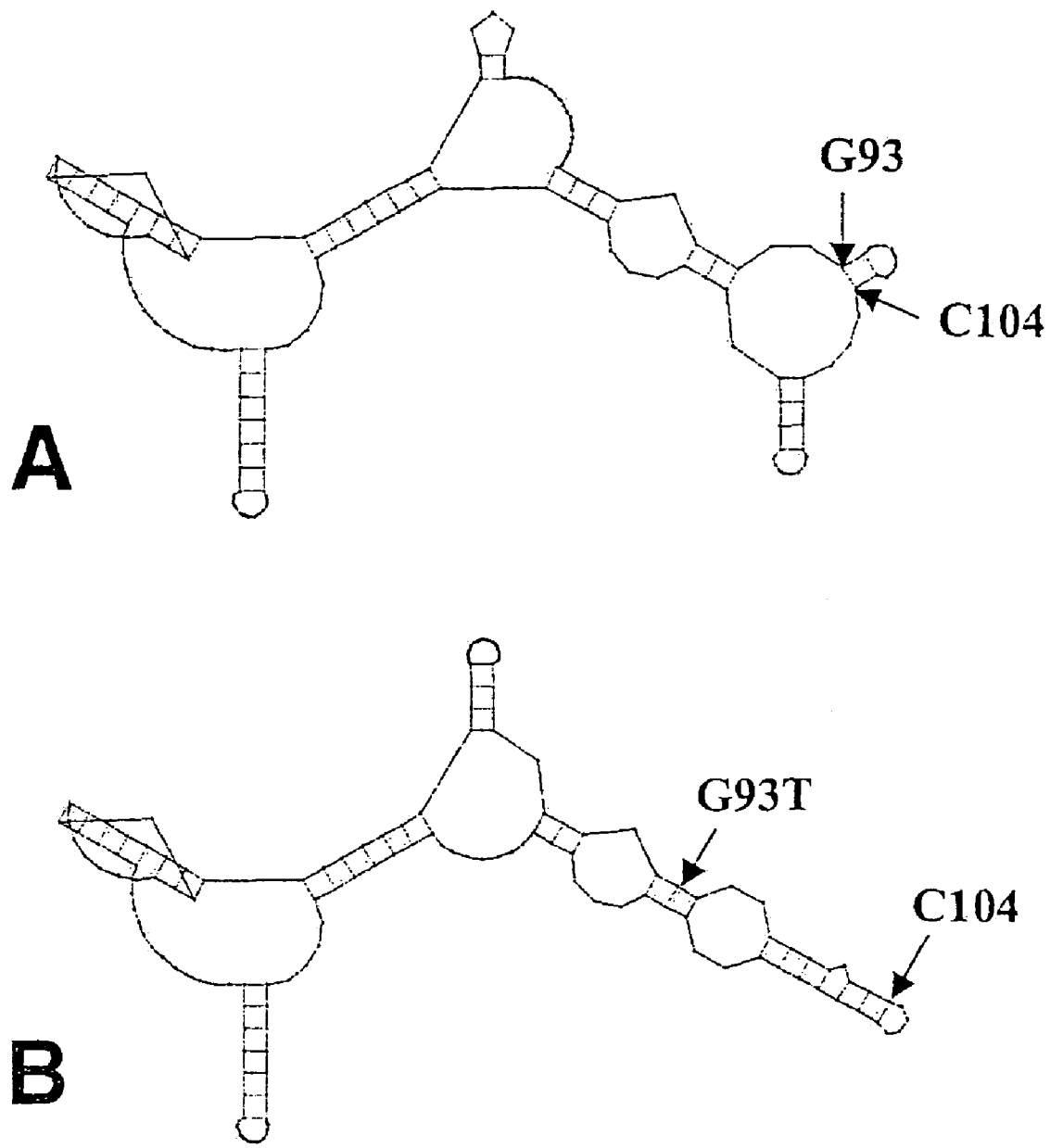
FIG. 5A and 5B is a diagram showing the predicted secondary structure of normal (FIG. 5A) and point-mutated (FIG. 5B) (G93T) MIR. The left portion of the structure is identical in normal and mutant RNAs; however, there is a significant difference between normal and mutant RNAs in the right portion of the structure.

In other applications, variant MIR-encoding nucleic acids encoding MIR that display substantial changes in structure can be generated by making nucleotide substitutions that cause less than conservative changes in the encoded polyribonucleotide. Examples of such nucleotide substitutions are those that cause marked changes in the secondary structure of the polyribonucleotide, or the capacity of the MIR to interact with a MIR-binding protein. Any such substantially changed variant MIR-encoding nucleic acid is included within the invention so long as it encodes a MIR having a secondary structure consistent with retention of a MIR biological activity, such as binding to one or more MIR-binding proteins. Examples of impermissible MIR variants can be found empirically, for example by testing the capacity of a selected variant to bind MIR-binding proteins in an assay such as a gel shift assay. As one example, a variant MIR-which lacks such bioactivity is a 166 nt fragment of MIR containing a G to C point mutation in position 93 of the sequence (G93T), encoded by the nucleic acid shown herein as SEQ ID NO:4 (see FIG. 3). The predicted secondary structure of the normal and mutant MIR are illustrated in FIG. 5.

Naturally occurring allelic variants of a native MIR-encoding nucleic acid within the invention are nucleic acids isolated from human, murine, ovine and axolotl tissue that have at least 75% (for example, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%) sequence identity with a native MIR-encoding nucleic acid, and encode MIR molecules having structural similarity to a native MIR. Homologs of a native MIR-encoding nucleic acid within the invention are nucleic acids isolated from other species that have at least 75% (for example, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%) sequence identity with a native MIR-encoding nucleic acid, and encode polyribonucleotides having structural similarity to native MIR. Public and/or proprietary nucleic acid databases can be searched in an attempt to identify other nucleic acid molecules having a high percent (for example, 70, 80, 90% or more) sequence identity with a native MIR-encoding nucleic acid.

Non-naturally occurring MIR-encoding nucleic acid variants are nucleic acids that do not occur in nature (for example, are made by the hand of man), have at least 75% (for example, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%) sequence identity with a native MIR-encoding nucleic acid, and encode polyribonucleotides having structural similarity to a native MIR RNA. Examples of non-naturally occurring MIR-encoding nucleic acid variants are those that encode a fragment of a MIR, those that hybridize to a native MIR or a complement of a native MIR under stringent conditions, and those that share at least 65% (for example, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%) sequence identity with a native MIR-encoding nucleic acid.

Nucleic acids encoding fragments of a native MIR-encoding nucleic acid within the invention are those that encode, for example, 10, 20, 30, 40, 50, 60, 70, 80, 90, 100, 110, 120, 130, 140, 150,160, 200, 250, 300, 350, 400, 450, 500, 550, 600 or more nucleotides of a native MIR, up to the full length sequence of about 620 nucleotides. Any fragment of a native MIR capable of binding a MIR-binding protein may be used. Shorter oligonucleotides (for example, those of 6, 7, 8, 9, 10, 11, 12, 13, 14, 15, 16, 17, 18, 19, 20, 30, 50, 100 base pairs in length) that encode or hybridize with nucleic acids that encode a native MIR or fragment thereof can be used as probes, primers, or anti-sense molecules. Longer polynucleotides (for example, those of 125, 150, 175, 200, 225, 250, 275, 300, or more base pairs) that encode or hybridize with nucleic acids that encode fragments of a native MIR can also be used in various aspects of the invention. As an example, a nucleic acid that encodes the bioactive 166 bp sequence shown as SEQ ID NO: 1 can be used, and can be obtained using PCR primers designated herein as SEQ ID NOS:2 and 3. Other MIR-encoding nucleic acids within the invention are longer fragments, for example between about 167 and about 620 nucleotides in length that contain SEQ ID NO:1 within their sequences, or MIR-encoding nucleic acids (for example MIR genes) greater than 620 nucleotides in length that include SEQ ID NO:5 within their sequence.

Nucleic acids encoding fragments of a native MIR can be made by enzymatic digestion (for example, using a restriction enzyme) or chemical degradation of a full length native MIR nucleic acid or variant thereof. The nucleic acids of the invention can be modified at the base moiety, sugar moiety, or phosphate backbone, for example, to improve stability of the molecule, hybridization, etc.

MIR-Binding Proteins

The MIR molecules of the invention have been shown to specifically binds to MIR-binding proteins present in cells undergoing differentiation to a cardiac muscle phenotype. The discovery of the interaction of MIR with MIR-binding proteins holds great promise for inducing a cardiac muscle phenotype in a cell through use of MIR and its interacting proteins. Any protein can be used that specifically binds to MIR, leading to the induction of a cardiac muscle phenotype in a cell containing that protein. MIR-binding proteins can be isolated and identified by techniques known in the art, and further described herein. MIR-binding proteins in a cell or tissue can be separated for example in a first step by two-dimensional polyacrylamide gel (2D gel) electrophoresis, one of the most powerful methods to resolve complex protein mixtures. Although 2D gels are currently a widely used separation tool, reverse phase HPLC, capillary electrophoresis, isoelectric focusing and related hybrid techniques can also provide powerful means of resolving complex protein mixtures, and might also be used in the invention.

In a second step, using a technique such as "Northwestern" blot analysis, the separated proteins can be tested for ability to bind to MIR, which is generally labeled with a detectable substance. Where a radioactive label is used as a detectable substance, a MIR-binding protein of the invention may be detected by autoradiography. The results of the autoradiography reveal those proteins separated within the 2D gel, i.e., "MIR-binding proteins," that display specific binding to the labeled MIR. Quantitation of the binding can be achieved by various optical methods. Confirmation of the specificity of the RNA-protein binding can be accomplished using a method such as a gel shift assay, in which binding of the radiolabeled MIR RNA to the protein is competitively challenged with increasing concentrations of unlabelled ("cold") MIR. Disappearance of a radioactive band representing a MIR:MIR-binding protein interaction in a dose-dependent manner is indicative of specific binding between the RNA and the protein.

In preferred embodiments of the method, MIR-binding proteins can have MWs of ~11-13 kDa and ~28-30 kDa. As shown in examples herein, alkaline MIR-binding proteins of these sizes were identified by Northwestern blotting using radiolabeled MIR as a probe of protein extracts from embryos undergoing cardiac morphogenesis.

Method of Inducing a Cardiac Muscle Phenotype in a Cell

In another aspect, the invention provides a method for inducing a cardiac muscle phenotype in a cell. The method includes the steps of: (a) providing a cell including at least one MIR-binding protein; and (b) contacting the cell with at least one MIR that specifically binds to at least one MIR-binding protein, in an amount sufficient to induce a cardiac muscle phenotype in the cell. The cardiac muscle phenotype can include rhythmic contraction of the cell, and formation of myofibrils.

Several parameters may be used to assess the amount of MIR sufficient for induction of a cardiac muscle phenotype in a cell. Functional criteria can be utilized, such as the induction of rhythmic contraction in a treated cell in culture, or the onset of beating of the heart in an animal model of cardiogenesis. In this regard, the Mexican axolotl, *Ambystoma mexicanum* provides a particularly useful animal model of cardiac cell differentiation, in that, as disclosed herein, failed cardiac cell differentiation and heart formation in a mutant strain of this species (exhibiting a G to T point mutation at position 93 of the MIR sequence) has been found to be correlated with failed interaction of the mutant MIR with a MIR-binding protein.

Besides functional parameters, morphological and immunohistochemical criteria can be used in determining the amount of MIR RNA sufficient for induction of a cardiac muscle phenotype in a cell. For example, detection of expression of markers of a cardiac cell phenotype, such as tropomyosin, is highly informative. As shown in examples herein, examination of the distribution of tropomyosin in cells in culture or whole mounts of developing embryos at intervals following treatment with MIR RNA can provide information as to the extent of rescue of normal cellular and organ structure, or the extent of development of a cardiac cell phenotype.

Cells Expressing MIR-Binding Proteins

The method of inducing a cardiac muscle phenotype in a cell includes the step (a) of: providing a cell including at least one MIR-binding protein. In theory, any cell that expresses a MIR-binding protein can be used in the method. The cell can be either a cell that endogenously expresses a MIR-binding protein, or cell that is caused to express a MIR-binding protein, for example by transduction with a vector containing a nucleic acid encoding a MIR-binding protein. Cellular sources of MIR-binding proteins can be identified by methods such as Northwestern blotting using MIR RNA as a probe, as described above. Alternatively, for MIR-binding proteins for which the nucleotide and amino acid sequences have been determined, nucleic acid and antibody probes can be developed and used for detection of MIR-binding proteins in cells and tissues by well-known techniques such as PCR, Northern blotting, Western blotting, immunodetection protocols and the like. Preferred cell types expressing MIR-binding proteins of use in the method can to be those of the cardiac lineage, such as cardiomyocytes, skeletal or smooth muscle cells, precardiac mesoderm cells, or stem cells that can be induced to differentiate along a pathway resulting in a cardiac cell phenotype. For promoting a cardiac cell phenotype in a cell to be used in a human, for example in a cell transplanted into the heart of a human, preferred cells are those derived from human tissues.

Contacting a Cell with MIR

The method of inducing a cardiac muscle phenotype in a cell includes the step (b) of contacting the cell with at least one MIR molecule that specifically binds to at least one MIR-binding protein, in an amount sufficient to induce a cardiac muscle phenotype in the cell. In some embodiments, the at least one MIR molecule can be encoded by a nucleic acid including a sequence that shares at least 75% sequence homology with SEQ ID NO:1. The MIR-encoding DNA, or MIR molecules can be obtained from a mammal, for example from the heart of an adult sheep.

The nucleic acid molecules of the invention find therapeutic applications in treatment, repair and regeneration of damaged heart muscle. For example, by direct injection of MIR, or by delivery of MIR by gene therapy using a vector-based delivery system, MIR can be introduced into an infarcted area after a heart attack. In an alternative approach involving transplantation, cells expressing a cardiac muscle phenotype can be used, for example, to repopulate damaged heart muscle. Such cells can be generated in vitro using the compositions and methods of the invention by introducing MIR, or vectors that drive MIR expression, into cell cultures for purposes of inducing heart cell differentiation in the cells. As an example, MIR or MIR-expressing vectors can be used in vitro to induce stem cells to differentiate along a cardiac phenotypic pathway. Such cells, propagated in vitro, have the potential to provide an unlimited source of heart muscle cells for use in animal subjects including human patients. Besides various forms of stem cells (for example those derived from embryonic, umbilical cord, or adult tissues such as bone marrow or blood), other cell types suitable for contact with MIR or MIR-encoding vectors include but are not limited to those of the cardiac lineage, such as cardiomyocytes, muscle precursor cells such as C2C12 skeletal or smooth muscle cells, precardiac mesoderm cells.

Several methods for introducing a MIR molecule into a host cell are within the scope of the invention. Methods involving physical techniques for the introduction of a MIR into a host cell can be adapted for use in the present invention. In some instances, as in examples described herein, MIR can be added directly to the cell, for example a cell within a heart. In a subject, for example a human, one delivery approach involves direct injection of in vitro synthesized MIR into the pericardial cavity.

Alternatively, cell electro-permeabilization (also termed cell electroporation) may be employed for MIR delivery into cells such as cultured cells. This technique involves the application of pulsed electric fields to cells to enhance cell permeability, resulting in transit of exogenous polynucleotide across the cytoplasmic membrane.

In one embodiment of the method, step (b) includes contacting the cell with MIR molecules and a liposome. RNA molecules such as MIR (as well as proteins) can be introduced into a cell by liposome-mediated uptake (See, generally, Hofland H E J and Sullivan S M, J Liposome Res 7: 187-205, 1997; and regarding transfer into heart cells, Zajdel R W et al. Anat Embryol 201:217-228, 2000). Cationic amphiphiles, including lipopolyamines and cationic lipids, may provide MIR transfer into target cells. Preformed cationic liposomes or cationic lipids may be mixed with plasmid DNA to generate cell-transfecting complexes. Suitable methods can also include use of cationic liposomes as agents for introducing RNA into cells.

Gene Therapy Using Vectors Expressing MIR-Encoding Nucleic Acids

As described above, the present invention further includes delivering MIR into a subject, by means of gene therapy technologies. Methods and compositions involving gene therapy vectors are generally known in the art and are described in methodology references such as Viral Vectors, eds. Yakov Gluzman and Stephen H. Hughes, Cold Spring Harbor Laboratory Press, Cold Spring Harbor, N.Y., 1988; Retroviruses, Cold Spring Harbor Laboratory Press, Plainview, N.Y., 2000; Gene Therapy Protocols (Methods in Molecular Medicine), ed. Jeffrey R. Morgan, Humana Press, Totawa, N.J., 2001. In this version of the method, step (b) includes contacting the cell with a vector that includes a nucleic acid that encodes at least one MIR molecule.

Non-viral methods of use in gene therapy are described, for example, in Nishikawa and Huang, Human Gene Ther. 12:861-870, 2001. For instance, techniques employing plasmid DNA as a vector for the introduction of a MIR into a cell are encompassed by the invention. Such techniques are generally known in the art and are further described in references such as Ilan, Y, Curr Opin Mol Ther 1:116-120, 1999, Wolff, J A, Neuromuscular Disord 7:314-318, 1997.

A further related aspect of the invention is a vector that includes a purified nucleic acid that encodes a MIR molecule having at least one functional activity of a native MIR molecule. Natural or synthetic nucleic acids encoding a MIR can be incorporated into recombinant nucleic acid constructs, typically DNA constructs, capable of introduction into and replication in a host cell. Some versions of the vector further include a second nucleic acid in the construct, for example a nucleic acid encoding a MIR-binding protein. Such a construct preferably is a vector that includes a replication system and sequences that are capable of driving expression of the nucleic acid(s). Appropriate transcriptional control sequences are included in the vector to allow it to be expressed in a cell. Expression of the cloned sequences occurs when the expression vector is introduced into an appropriate host cell. If a eukaryotic expression vector is employed, then the appropriate host cell would be any eukaryotic cell capable of expressing the cloned sequences. Suitable cells for use in the invention are further described below.

Many vectors suitable for transformation of animal cells are known. (See, for example, Pouwels et al., Cloning Vectors, A Laboratory Manual, 1985, Supp. 1987, Elsevier Health Sciences; and Glover, D M, DNA Cloning 2: Expression Systems, 1995, Oxford University Press.) Typically, animal expression vectors include (1) one or more cloned animal genes under the transcriptional control of 5' and 3' regulatory sequences and (2) a dominant selectable marker. Selectable marker gene are used to identify the cells that have become transformed. Suitable selectable marker genes include genes encoding enzymes that produce antibiotic resistance (for example, those conferring resistance to hygromycin, kanamycin, bleomycin, neomycin, and streptomycin).

Such animal expression vectors may also contain, if desired, a promoter regulatory region (for example, a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

A preferred viral expression vector of use for transfection of the MIR gene into heart cells is Adeno-Associated Virus (AAV). Use of this vector is advantageous from the standpoint of its demonstrated high level of safety in human subjects. In another embodiment, a preferred vector is pSIREN-Shuttle (BD Sciences Clontech) which can be used to deliver MIR-encoding nucleic acids by liposome-mediated methods. Advantageously, this vector can transiently express a viral genomic transcript containing the human U6 promoter and MIR. This vector can be used directly, or in conjunction with the BD Adeno-XExpression System (BD Sciences Clontech, La Jolla, Calif., Cat. No. 631513; 1) or its Accessory Kits (Cat. Nos. 631026 & 631027). In addition to the foregoing vectors, other viral vectors can be adapted for use in the invention, for example lentiviral vectors.

An example of a useful promoter which could be used to express a MIR-encoding nucleic acid according to the invention is a cytomegalovirus (CMV) immediate early promoter (CMV IE) (Xu et al., Gene 272: 149-156, 2001). These promoters confer high levels of expression in most animal tissues, and are generally not dependent on the particular encoded proteins to be expressed. Other promoters that may be useful in the invention can include the *Rous sarcoma* virus promoter, adenovirus major late promoter (MLP), herpes simplex virus (HSV) promoter, HIV long terminal repeat (LTR) promoter, mouse mammary tumor virus LTR promoter, β-actin promoter, or the murine metallothionein promoter (Stratagene San Diego Calif.). Synthetic promoters, hybrid promoters, and the like may also be useful in the invention and are known in the art.

The promoter may be constitutive or regulatable. Constitutive promoters are those which cause an operably linked gene to be expressed essentially at all times. Regulatable promoters, by contrast, are those which can be activated or deactivated. Regulatable promoters include "inducible" promoters, which are usually "off" but which may be induced to turn "on," and "repressible" promoters, which are usually "on," but may be turned "off." Many different regulatable promoters are known, including those regulated by temperature, hormones, heavy metals, the product of the gene, regulatory proteins, and antibiotics such as doxycycline. These distinctions are not absolute; a constitutive promoter may be regulatable to some degree. Hybrid promoters may be constructed in which the operator of one promoter is transferred into another.

The promoter may be a ubiquitous promoter, active in essentially all cells of the host organism, for example, the β-actin promoter, or it may be a promoter whose expression is more or less specific to the target cells, such as cells of the myocyte lineage. For specific expression of MIR in muscle cells, several promoters can be incorporated into the vector construct. As examples, muscle specific promoters such as the alpha-myosin heavy chain gene promoter (Sanbe A et al., 2003) or the chicken cardiac actin promoter (Sepulveda J L et al., 2002) can be used to drive MIR expression specifically in cardiac muscle cells.

EXAMPLES

The following examples serve to illustrate the invention without limiting it thereby. It will be understood that variations and modifications can be made without departing from the spirit and scope of the invention.

Example 1

Organ Culture System For Heart Morphogenesis

Animals. Adult Mexican axolotls were maintained in the axolotl colony at Florida Atlantic University, Boca Raton campus, Florida. Animals were kept in aquaria in dilute Holtfreter's solution and fed salmon pellets, raw liver and live earthworms. Normal and cardiac mutant axolotl embryos were obtained from matings between homozygous normal (+/+×+/+) or heterozygous (+/c×+/c) animals. Some embryos used in the study were obtained from the axolotl colony at Indiana University, Bloomington, Ind.

Organ culture system. Stage 34 embryos were removed from their jelly coats and identified as normal or mutant on the basis of possessing a beating heart. To remove the heart, embryos were placed in Steinberg's solution (Zackson and Steinberg, 1986) consisting of 0.06 mM NaCl, 0.6 mM KCl, 0.3 mM $CaCl_2$, 0.8 mM $MgSO_4 \cdot 7 H_2o$, 10 mM HEPES, pH 7.4, with 1% antibiotic/antimycotic (containing 10,000 units penicillin, 10,000 μg streptomysin, and 25 μg amphotericin B) and filter-sterilized (through a 0.22 μm Nalgene filter unit) before use. Embryos in this buffer were dissected in Petri dishes lined with modeling clay. The clay facilitated manipulation and allowed restraint of the embryos in position during dissection. The epidermis was peeled away from the pharyngeal region exposing the heart. The heart was extirpated with forceps and placed in 10 μl drops of Steinberg's solution (either alone or with 0.4 mg/ml RNA) in a sterile 60 mm Petri dish lined with dental wax or parafilm.

Conditioned medium (CM). CM was prepared by culturing anterior endoderms from stage 25 normal, wild-type embryos in clusters of ten explants/100 μl Steinberg's solution. Endoderm cultures were maintained for 48 hrs, and the CM was harvested following centrifugation to eliminate cellular debris. All cultures were kept at 17° C. for the duration of the culture period.

In vitro bioassay. Assays of "rescue" of cardiac lethal mutant hearts was performed as follows. Non-beating whole mutant hearts and beating whole normal hearts as controls were explanted into small (10 μl) droplet cultures of Steinberg's buffered salt solution. This simple culture system, without the requirement of complex nutrient additives is advantageous for testing the activity of added RNA without interference from medium components. Liposome-mediated delivery of exogenous nucleic acids into the whole embryonic hearts was used to deliver the RNA as previously described (Zajdel et al., 2000). Liposome reagents (Lipofectin, Gibco) were diluted in Steinberg's solution to a final concentration of 0.1 μg/ml. Various heart samples were collected at selected intervals for confocal and electron microscopic examination.

Example 2

Treatment of Embryonic Hearts with RNA from Adult Sheep Hearts

RNA extraction. RNA was extracted from adult sheep heart and control tissues using the acid guanidinium isothiocyanate-phenol-chloroform method described by Chomczynski and Sacchi (1987). Briefly, frozen tissues were homogenized in a denaturing solution containing guanidinium isothiocyanate. The mixture was extracted with equal volumes of phenol: chloroform: isoamyl alcohol and spun in a centrifuge. The aqueous phase was recovered, extracted once with chloroform:isoamyl alcohol, and the RNA precipitated overnight with sodium acetate/ethanol at −20° C. The RNA mixture was centrifuged at 4° C. and the precipitate was dissolved in DEPC-treated water. The concentration and purity of the RNA was determined by spectrophotometry. The $A_{260}/A_{280}$ ratios were always above 1.8, indicating minimal contamination of the RNA with protein. Prior to addition to cultures, RNA was lyophilized and resuspended in sterile Steinberg's solution at a concentration of 0.4 mg/ml (Davis and Lemanski, 1987). Some samples of RNA were pre-treated with RNase prior to use. (RNAOUT, 10 units/30 μl, Promega) for 20 minutes before applying to the mutant hearts.

Mutant hearts from stage 35 embryos were obtained and prepared as explant cultures as described above. Control cultures were incubated sheep heart RNA, RNase pre-treated sheep heart RNA, (at a concentration of 40 ng/10 μl in Steinberg's solution) or with Steinberg's medium alone. Positive controls included RNA from CM and sense clone #4 RNA, described previously (Lemanski et al., 1996). Cultures were maintained for up to 10 days, and fixed at intervals starting at 48 hr after RNA addition.

Example 3

Immunostaining of Myofibrils in Heart Wholemounts

Hearts were fixed as previously described (Lemanski, 1979). All steps were performed at room temperature with gentle agitation on an orbital shaker. Hearts were placed in 1 mM DTSP (Sigma Co. St. Louis, Mo.) dissolved with 1% dimethylsulfoxide in Steinberg's solution for 15 min. Further permeabilization occurred in 0.5% Nonidet P-40 in Steinberg's solution for 15 min. The reaction was quenched by two 10-min washes in 0.1M glycine. After blocking with 3% bovine serum albumin (BSA) in Steinberg's solution containing 0.05% Tween-20 for 1 h, the hearts were incubated with CH1 monoclonal anti-tropomyosin antibody (Lin et al. 1985) diluted to 1:50 in Steinberg's solution for 1 hr and washed several times. Hearts were then incubated in Oregon green-conjugated anti-mouse antibody (Molecular Probes, Eugene, Oreg.) at a 1:50 dilution for 45 min. The hearts were rinsed in several changes of BSA in Steinberg's solution and post-fixed in 2% paraformaldehyde for 30 min. The fixation was quenched by 0.1 M glycine for 30 min and placed in Steinberg's solution.

Example 4

Light and Electron Microscopy of Heart Wholemounts

Confocal microscopy. Following immunostaining, whole hearts were mounted on glass slides in 50% glycerol/phosphate buffered saline containing 2% n-propyl gallate (Lemanski et al., 2001). To prevent crushing of the hearts, three layers of fingernail polish were used to support the glass coverslips. Specimens were viewed on a Biorad 2100 confocal laser scanning microscope. Fluorescence was excited at 488 nm. A 30 section z-series (1 μm thickness for each section) was made for each sample and system software was used to display the final image on a monitor. Color photographs were printed from the latter on Ilfochrome Classic Deluxe CLM 1 k paper.

Electron microscopy. Normal, untreated mutant, and corrected mutant hearts were fixed in a glutaraldehyde-formaldehyde-picric acid mixture, buffered to 7.4 with 0.1 M phosphate buffer (Ito and Kamovsky, 1968) for 1 hr at room temperature. Hearts were post-fixed in 1% osmium tetroxide in the same buffer for 60 min, dehydrated in a graded series of ethanol solutions, and embedded in Epon or Araldite in flat molds. Ultrathin 50-70 nm sections were cut, stained with uranyl acetate and lead citrate, and viewed in a JEOL 100 CX II electron microscope at an acceleration of 80 kV.

Example 5

Rescue of Mutant Heart Function by Sheep Heart RNA

The ability of adult sheep heart RNA to produce a rescue effect on mutant axolotl hearts was tested using methods described above. The results showed that adult sheep heart RNA was able to rescue mutant hearts. Within 48 hrs of culture in the presence of this RNA, the mutant hearts developed vigorous rhythmic beating throughout their lengths. Mutant hearts cultured as controls, i.e., either in Steinberg's solution without RNA or with RNase pre-treated sheep heart RNA, did not beat throughout their lengths, even after 10 days of incubation. Normal control hearts, in either Steinberg's solution alone or with RNA, continued to beat throughout the culture period. Results of the heartbeat assays are summarized in Table 1.

TABLE 1

Correction of Mutant Axolotl Hearts with Mammalian MIR

| RNA Type | Number of Corrected hearts | Total Number of Hearts | % Corrected |
|---|---|---|---|
| Sheep heart RNA | 26 | 26 | 100 (by tropomyosin) |
|  | 21 | 38 | 55* (by beating) |
| RNase-treated sheep heart | 0 | 19 | 0 (by beating) |
| RNA | 0 | 30 | 0 (by tropomyosin) |
| Conditioned Medium RNA | 19 | 30 | 63* (by beating) |
| Sense Clone #4 RNA | 22 | 22 | 100 (by tropomyosin) |
|  | 19 | 24 | 79* (by beating) |
| Antisense Clone #4 RNA | 0 | 19 | 0 (by beating) |
| Axolotl liver RNA♥ | 0 | 12 | 0 (by beating) |
| Steinberg's solution only | 0 | 30 | 0 (by tropomyosin) |
|  | 0 | 30 | 0 (by beating) |

By tropomyosin: Correction is based on tropomyosin expression by confocal microscopy.
By beating: Correction is based on beating of hearts.
* = P < or = .01 when compared to controls of Steinberg's solution only.
All types of RNA used were at 40 ng/ 10 μL except for ♥: axolotl liver RNA, which was used at 5 μg/ 10 μL (Data from Davis and Lemanski, 1987).
Clone #4 RNA is described in Lemanski et al., 1996.

Example 6

Rescue of Myofibrillogenesis in Mutant Hearts By Sheep Heart RNA

Immunostaining of tropomyosin. Normal and mutant hearts were cultured as described above. Mutant hearts were incubated for 10 days with either positive control RNA (axolotl embryonic endoderm RNA), sheep heart RNA, or RNase-treated sheep heart RNA, followed by fixation and immunostaining. Referring to FIG. 1, the results showed significant tropomyosin staining, and well organized sarcomeric myofibrils in the normal hearts, indicative of a high level of differentiation (FIG. 1A). A very similar pattern of staining was observed in the majority of the heart cells in the ventricular area in mutant hearts treated with either control RNA or adult sheep heart RNA (FIGS. 1B, C). In contrast, tropomyosin expression and myofibrillogenesis was not observed in mutant hearts treated with RNase-treated sheep heart RNA (FIG. 1D). This finding demonstrated that the functional unit in the adult sheep heart responsible for mutant heart rescue is RNA.

Electron microscopy. The data from electron microscopy were consistent with the confocal microscopic results. Normal control hearts, incubated in either Steinberg's solution alone or with the RNA showed well-organized myofibrils by electron microscopy. Normal hearts cultured in RNA-enriched media presented no apparent differences from those cultured in Steinberg's solution alone. Examination of control cardiomyocytes from an organ-cultured normal heart revealed the presence of sarcomeric myofibrils complete with z lines.

In EM images of non-beating mutant hearts organ-cultured in Steinberg's solution without RNA, organized sarcomeric myofibrils were not discernable. Instead, amorphous proteinaceous collections were seen beneath the sarcolemma as well as a few filamentous structures. In sharp contrast, electron micrographs of cardiomyocytes from mutant hearts organ-cultured with RNA from adult sheep heart revealed organized myofibrils of normal ultrastructural morphology after two days in culture, as well as evidence of early stages of myofibrillogenesis. Rescued mutant hearts showed distinct but disarrayed myofibrils in the cells, characteristic of early normal stages of myofibril development in axolotl cardiac cells (Lemanski, 1979). Myofibrils with thick and thin filaments were visible in the rescued cells. In favorable planes of section, it was also possible to distinguish A-bands, I-bands, and M-line areas. The "rescued" mutant myofibrils were morphologically indistinguishable from normal.

Example 7

Methods for Analysis of RNA Mediating Mutant Heart Rescue

RT-PCR. Total RNA was extracted from axolotl embryos at different stages by using Tri Reagent™ (Sigma) and all steps were carried out according to the manufacture's instructions. The extracted RNA was incubated with RNase-free DNase (Promega, Inc. Madison, Wis.). After treatment, 1 μg RNA was used for first reverse transcription with random hexamer primers. A 166 nt MIR sequence termed Clone #4 RNA has been previously described (Lemanski et al., 1996; Genbank Accession No. U87267) and is herein designated as SEQ ID NO:1. A PCR reaction was performed to amplify this sequence using a reverse primer 5'-GTGT-TCTTTCTGGGCTCCATTC-3' (SEQ ID NO:2) and a forward primer 5'-AGCACCACTCCATTTTTGGAACAC-3' (SEQ ID NO:3) based on this sequence. The TaqBead System (Promega, Madison, Wis.) was used for the amplification. The PCR products were analyzed by electrophoresis and confirmed by Southern blotting using a specific MIR cDNA probe prepared using the original 166 nt sequence as template and randomly labeled with a DIG Starter II Kit (Roche, Inc., Indianapolis, Ind.).

Quantitative RT-PCR. After reverse transcription of adult tissue RNAs, together with ribosomal RNA gene primers, a pair of competitor primers (Ambion, Austin, Tex.) was used in the PCR reactions which competed with ribosomal RNA primers to lower the productivity of the cDNA. Preliminary assays were used to determine the ratio of competitor primers to PCR primers of ribosomal RNA gene suitable for achieving a linear range of PCR amplification that overlapped the range when amplifying the MIR RNA by RT-PCR alone. The cycle number (35 cycles) that was within this range was set up in PCR reactions in which the primer pairs of both genes (a mixture of ribosomal RNA gene competitor primers and ribosomal RNA PCR primers at the determined ratio [7.5:2.5] and MIR primers) were mixed together in one PCR reaction.

In vitro RNA synthesis. A MIR cDNA with T7 or T3 promoters at the 5' or 3' ends was made using the PCR reaction with fusion primers. After purification, the fused DNA (MIR with T7 or T3 promoters) was used as template for in vitro RNA synthesis with a T7, T3 MEGAshortscript kit (Ambion, Austin, Tex.). After DNase treatment, the synthetic RNAs were extracted with phenol/chloroform (pH4.0, Sigma) to remove proteins, precipitated by isopropanol (Sigma, St. Louis, Mo.) and dissolved in nuclease-free water. RNA was then quantitated by reading of the $OD_{260}$, adjusted to the concentration of 700 ng/ul, aliquotted and stored at −80° C.

Prediction of RNA secondary structure. RNA secondary structures of normal and mutant MIR RNA were predicted by Genebee software, an internet-based server for analyzing biopolymer structures (Brodsky et al., 1995). The method applied in this software for RNA secondary structure prediction uses phylogenetic considerations for energy optimization. Because no MIR homologous sequences have been identified, the RNA secondary structures generated by the software and chosen for comparison were based solely on the lowest energy (free enthalpy of the structure).

Example 8

Methods of Analysis of MIR-Interacting Proteins

Two-dimensional Northwestern blot analysis. Stage 15 axolotl embryos were homogenized and lysed by incubation for 20 min in 1 ml of ice-cold lysis buffer containing 20 mM Tris-HCI (pH 7.4), 150 mM NaCl, 1% Triton X-100, 1 mM phenylmethylsulfonyl fluoride, 0.15 U/ml aprotinin, 10 μg/ml leupeptin, 10 μg/ml pepstain A, I mM sodium orthovanadate, and 10% glycerol. The lysate was clarified by centrifugation at 14,000 g for 10 min at 4° C. Isoelectric focusing for the first dimension was performed on a MINI-PROTEAN II Tube Cell system (Biorad) following the manufacturer's protocol. Ten ug of protein samples was loaded onto the gel tubes and run at 500V for 10 minutes followed by 3.5 hours at 750V.

After the first dimensional run was completed, the tube gel was ejected by a syringe out onto a Parafilm laboratory film, overlaid with 200 ul SDS sample equilibration buffer (0.0625 M Tris HCI, pH 6.8, 2.3% SDS, 5.0% β-mercaptoethol, 10% glycerol, 0.00125% Bromophenol blue), and allowed to equilibrate for 10 minutes. The tube gel was placed between glass plates and onto the top of a 12.0% SDS slab gel. Samples were resolved by running a second dimensional SDS-polyacrylamide electrophoretic gel followed by transfer from the gel to a nitrocellulose membrane (Amersham) at 15 V for 30 min with a Trans-Blot semi-dry apparatus (Bio-Rad).

Transferred proteins were renatured overnight in a solution containing 15 mM HEPES, pH 8, 10 mM KCl, 10% glycerol, and 1 mM dithiothreitol at 4° C. Membranes were then incubated with radiolabeled MIR RNA ($5 \times 10^6$ cpm/ml, final concentration) for 1 h at 30° C. in renaturation buffer containing 2 mg/ml tRNA. Unbound RNA was removed by washing twice at room temperature with renaturation buffer, followed by autoradiography.

Gel shift assay. Bioactive RNA was synthesized as described above from MIR cDNA using T7 RNA polymerase in the presence of $^{32}$P-UTP. Homogenates were prepared as described for wo-dimensional Northwestern blot analysis from the following tissues: stage 15 normal embryos; adult tissues; and normal embryonic hearts from stages 35, 37, and 40. 5-15 µg protein was added to binding buffer (1.3 mM DTT, 2.66 mM MgCl$_2$, 13.3 mM HEPES pH 7.4, 133 mM KCl, 0.083 µg/µl yeast RNA and 50% glycerol) containing 40,000 cpm radio-labeled MIR or mutant MIR RNA. Hot RNA probe was prepared by T7 driven in vitro transcription using PCR generated templates of mutant and normal MIR. The RNA-protein mixture was incubated for 15 minutes on ice and then for 15 minutes at room temperature. The reaction mixtures were electrophoresed on pre-run 4% polyacrylamide gels in the presence of TBE (Tris-Borate-EDTA) buffer until the dye had migrated 75% of the length of the gel. The gels were subsequently dried and subjected to autoradiography.

Example 9

Analysis of MIR in Normal and Mutant Axolotls

Figure 2:
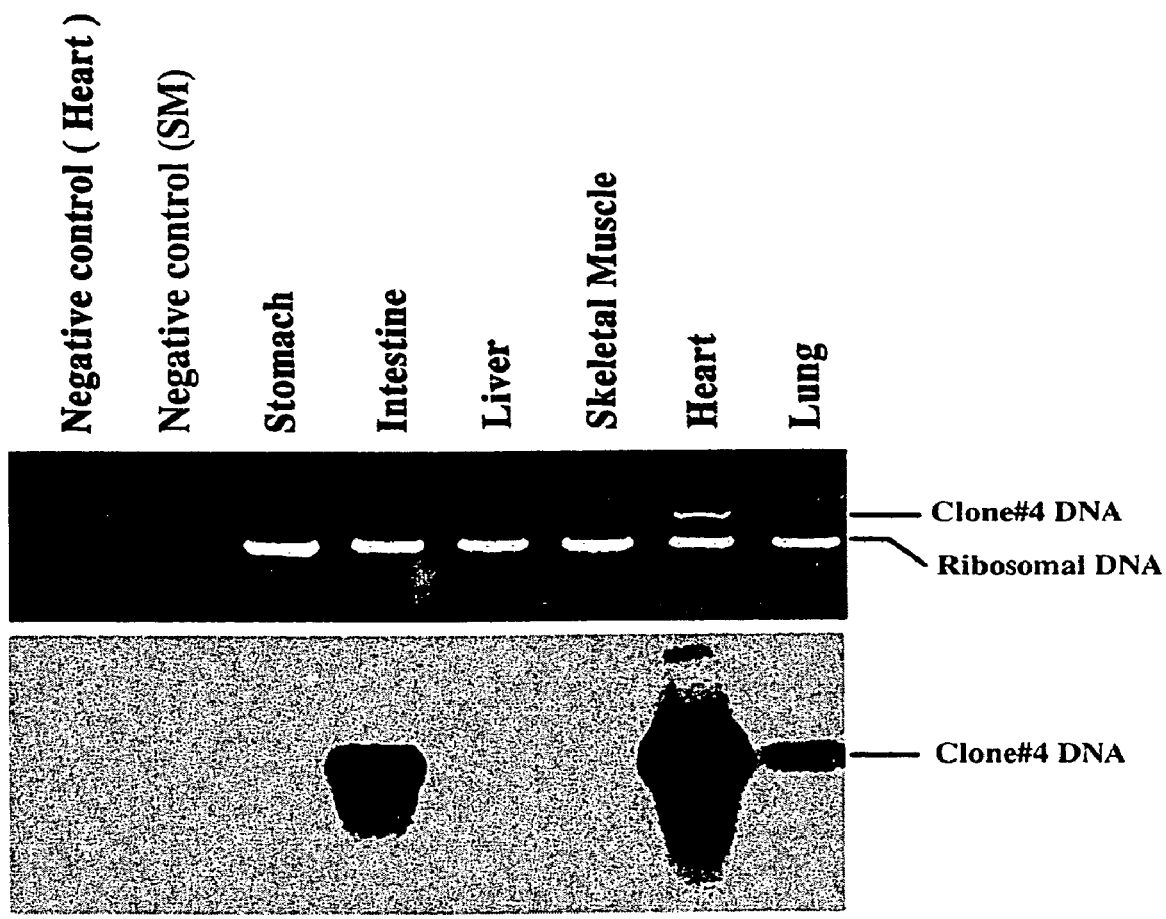
FIG. 2 shows quantitative RT-PCR of MIR expression in total RNA from various tissues of adult axolotls. Upper panel: agarose gel showing positive PCR product (upper band) only in heart. Ribosomal DNA (lower band), which is ubiquitously expressed in tissues, shows equal expression in all tested tissues. Lower panel: Southern blot probed with a MIR-specific cDNA probe. Very strong hybridization is seen with DNA from heart, with much lower levels detectable in intestine and lung, but absent in stomach, liver or skeletal muscle.

To compare the levels of MIR in normal and mutant axolotls, RT-PCR analyses were performed as described above using total RNA from normal (+/+) and mutant (c/c) axolotl embryos and amplification using MIR-specific primer pairs. PCR products were analyzed by electrophoresis and confirmed by Southern blotting with a MIR-specific cDNA probe at different stages of embryonic and adult development. Synthetic MIR was used as a positive control. Negative control was a PCR product obtained without RT from total RNA of stage 15 normal embryos. The results showed that MIR RNA expression starts at a very early stage of embryonic development (i.e., stage 15, early neurula) and continues to stages 20 through 30. MIR expression was still detectable in some adult tissues, being most abundant in the heart but also present in lung and gut, both of which are derivatives of embryonic endoderm, the heart induction tissue (FIG. 2). The results with normal embryos demonstrating presence of MIR RNA in axolotl embryos during neurulation when cardiogenic induction first takes place add further support to the concept that an RNA-mediated signaling event occurs during the onset of cardiogenesis. Results with mutant axolotl embryos showing a MIR expression pattern virtually identical to that of normal axolotl embryos in all stages examined indicated that the cardiac defect found in mutant embryos was not caused by absent or decreased MIR transcription.

Example 10

Point Mutation in MIR from Axolotl Heart Mutants

To compare the sequence and structure of normal and mutant MIR, a MIR cDNA was obtained by RT-PCR amplification of total RNA from normal and mutant embryos, subcloned and analyzed for determination of nucleotide sequence as described above. Sequencing of five clones each from three embryonic stages (i.e., stages 15, 20 and 30) revealed a point mutation (G to T) in mutant MIR cDNA. Alignment of the normal sequence (SEQ ID NO:1) and the mutant sequence (SEQ ID NO:4) is shown in FIG. 3. The consistent finding of the G to T mutation in sequencing results from repeated PCR reactions and numerous different spawnings excluded the possibility that the observed mutation was an artifact created during PCR amplification.

Example 11

Point Mutation in Mutant MIR RNA Prevents Cardiac Rescue

To investigate the biological effects of the observed point mutation in mutant MIR, bioassays were performed using the droplet incubation method described above in which mutant hearts were incubated with the normal and mutant RNA. Results showed that neither synthesized MIR RNA nor lipofectin caused significant damage to the embryonic hearts, since normal hearts incubated as controls for the same time with either MIR or lipofectin showed no abnormalities, and were still beating after 5 days of incubation.

Figure 4:
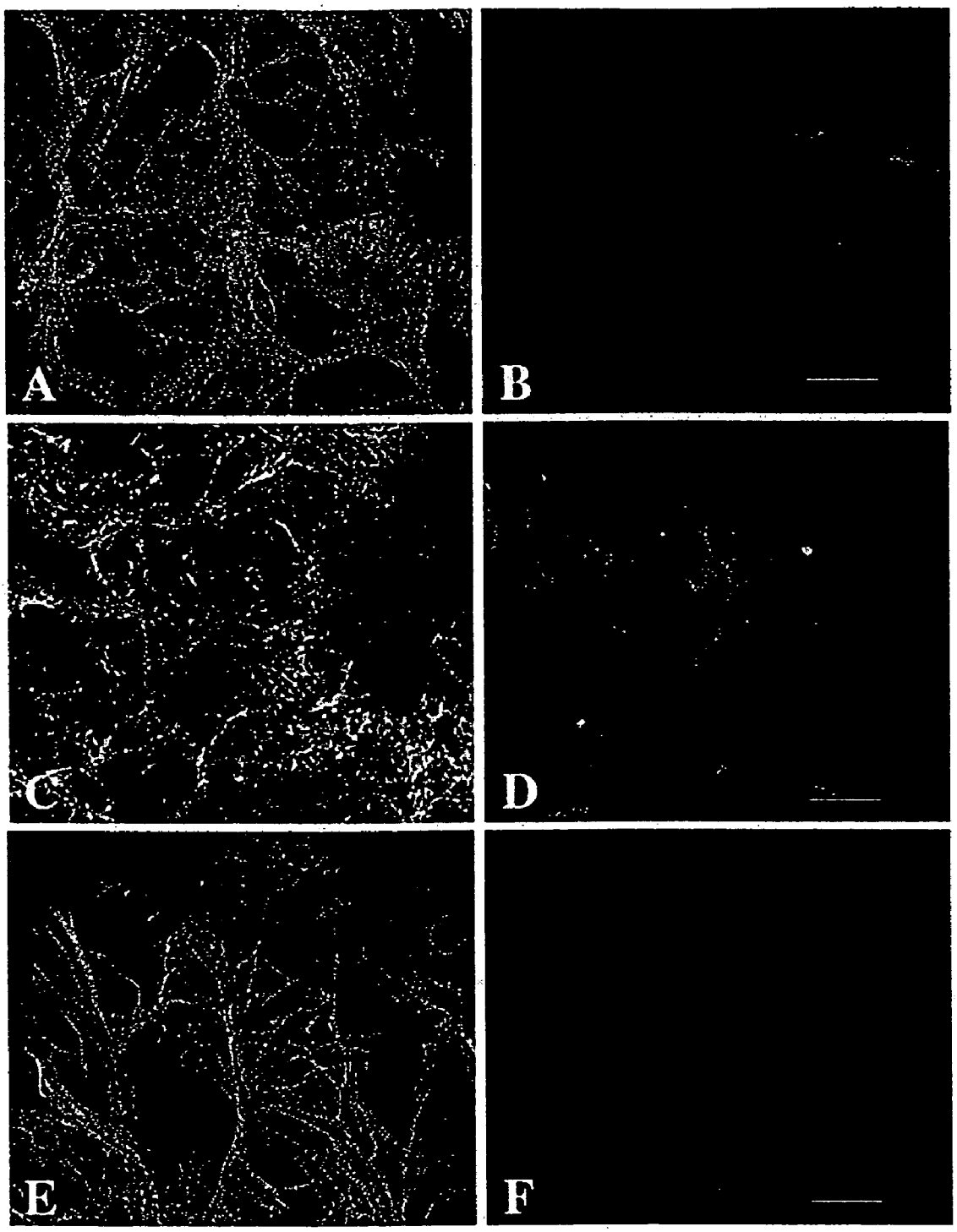
FIG. 4 shows confocal scanning microscopic images of normal and c/c mutant embryonic axolotl hearts subjected to in vitro bioassays, and immunostained with anti-tropomyosin antibodies. (A) Normal heart shows substantial tropomyosin staining. (B) Mutant heart exhibits very little staining for tropomyosin as compared to normal heart. (C) Rescued mutant heart organ-cultured for 2 days in the presence of normal MIR RNA. Tropomyosin is abundant. (D) Mutant heart cultured for 2 days in the presence of mutant MIR RNA. Very little staining for tropomyosin is observed in these hearts. (E) Rescued mutant heart after 4 day incubation with normal MIR. Tropomyosin distribution has changed to a more organized pattern compared with appearance at 2 days (Compare (C) and (E).) (F) Mutant heart after 4 days' exposure to mutant MIR shows no tropomyosin staining. Bar scale: 50 µm.

Following the RNA incubation period, normal, mutant and rescued mutant hearts were processed as described for immunofluorescent analysis of tropomyosin content and distribution and examined by confocal laser scanning microscopy. All hearts were fixed after either two or four days incubation with or without RNA. Referring to FIG. 4, normal hearts showed strong staining for tropomyosin with well-formed myofibrils (FIG. 4A). Mutant hearts showed very little staining for tropomyosin, with no evidence of highly organized myofibrils (FIG. 4B). After treatment with treated with normal (wild type) MIR RNA, 100% of the 17 mutant hearts were rescued as evidenced by significant tropomyosin staining and organized myofibrils in various areas of the cells after 2 days incubation (FIG. 4C). This result was further confirmed by electron microscopy. The organized pattern of myofibrils increased significantly in the cardiac myocytes of rescued mutant hearts after a longer time of incubation (i.e., 4 days), and appeared similar to normal (FIG. 4E). Controls using RNase treated RNA completely abolished the ability of MIR RNA to correct mutant hearts.

In marked contrast to the results using normal MIR RNA, no increase in tropomyosin staining or organized myofibrils was observed in 15 mutant hearts incubated with mutant MIR for either 2 days (FIG. 4D) or 4 days (FIG. 4F). This result demonstrated that the G93T the point mutation in the MIR molecule caused this RNA to lose its myofibrillogenesis-inducing bioactivity.

Example 12

Point Mutation in MIR Alters RNA Secondary Structure

While not intending to be bound to any particular theory, the inventors consider it unlikely that either the normal or the point-mutated RNA is translated into a peptide within heart cells. Rather it is thought to represent a bioactive RNA. Neither the normal nor mutant RNA exhibits typical sequences necessary for translation, including 5' capping, or a 3' poly (A) tail. Also, the bioactive MIR sequence can be relatively short (for example, about 166 nt), with no internal ribosomal entry site (IRES), which is generally considered to be ~450 nt in length (Pestova et al., 2001).

To determine whether the G93T point mutation in the mutant MIR alters the secondary structure of the RNA, secondary structure analysis was performed as described above using a GENEBEE software package. Referring to FIG. 5, the results of the analysis revealed significant structural differences between MIR RNA from normal axolotls and that from mutants. Distinctive three-dimensional structures in RNA molecules are well known. Such differences in secondary structure are very likely to impose functional differences on the interaction of normal and point-mutated RNAs with other molecules.

Example 13

Point Mutation in MIR Alters RNA-Protein Binding

Figure 6:
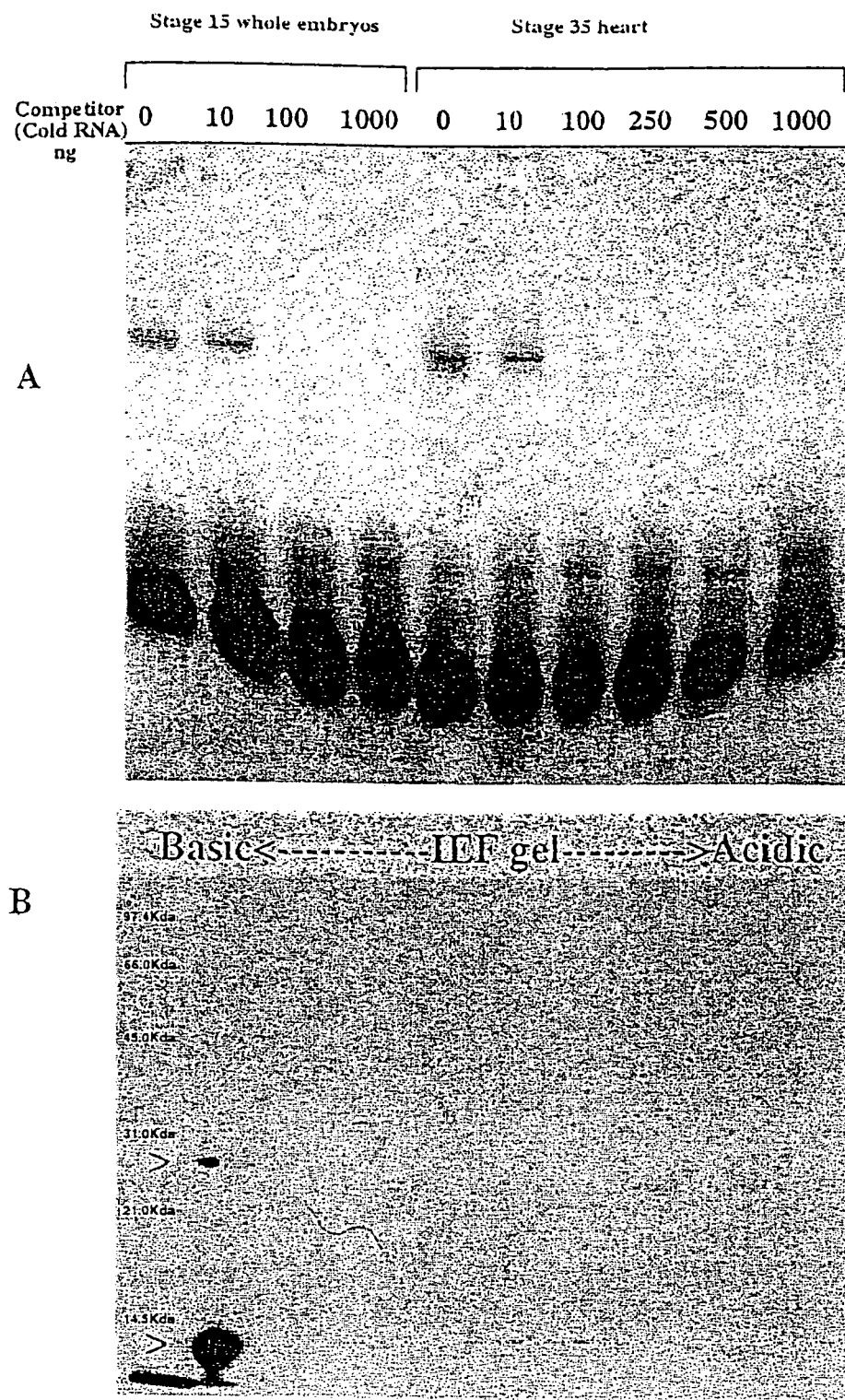
FIG. 6 is two autoradiograms showing gel shift competition assay (A) and Northwestern blot analysis (B). (A) Radio-labeled bioactive MIR was mixed with total protein from stage 15 normal axolotl embryos or stage 35 hearts. Binding of MIR (upper band) was competitively inhibited with increasing concentrations of cold MIR (0 to 1000 ng). (B) Northwestern blot showing two-dimensional gel electrophoresis of extract from stage 15 normal embryos, probed with $^{32}$P labeled MIR. MIR binds to two proteins (indicated by >) with MWs of ~28-30 and ~11-13 kDa.

Gel-shift assays were performed to examine the interaction of normal and mutant MIR with axolotl myocardial proteins. Following incubation with radio-labeled bioactive MIR, a band was observed using protein samples from stage 15 whole embryos or stage 35 hearts. Competition for binding with excess cold bioactive RNA removed the band in a dose-dependent manner, demonstrating that the bioactive RNA binds to axolotl proteins (FIG. 6A).

A Northwestern blot experiment was performed to further characterize the proteins binding with the MIR. As shown in FIG. 6B, MIR was found to bind to two alkaline proteins from whole axolotl embryos at stage 15 with a similar isoelectric point (~11). One of these proteins displayed a molecular weight (MW) of ~28-30 kDa, and the other was ~11-13 kDa. A more pronounced signal was observed for the lower MW protein. The results of the gel shift and Northwestern analysis demonstrated that in normal heart development, MIR-binding proteins were initially detectable at about stage 15 (early neurula) and remained detectable at least up to stage 35.

The point-mutated MIR from mutant embryos showed an altered binding pattern as compared to normal RNA when incubated with protein extract from whole embryos at stage 15-17. Both the binding pattern and the RNA migration rate were significantly changed. Whereas normal MIR RNA+ protein extract from normal (+/+) stage 15-17 whole embryos revealed the presence of an ~28-30 kDa binding protein described above, no corresponding binding was observed between this protein and the point-mutated MIR, even in heavily-loaded gels following lengthy overexposure of the autoradiogram. A faint band of protein-RNA complex with the lower MW protein species was visible in extracts incubated with mutant RNA. This result clearly demonstrated failure of binding of the larger MW protein by the point-mutated MIR RNA, a finding consistent with the existence of the altered secondary structure of the mutant RNA. The results taken together indicate that the larger MW protein may play a role in mediating the rescue ability of normal MIR. Through a binding interaction with another molecule, the larger MW protein, or the RNA-protein complex, could be activated to participate in the control of gene expression.

Example 14

Isolation of Nucleotide Sequence Encoding Full-length MIR

Starting from the 166 bp sequence of Clone #4 (SEQ ID NO:1; shown in FIG. 3), the nucleotide sequence encoding this RNA was extended. Primers were designed based on the known sequences using methods well known in the art of molecular biology. Genomic walking was performed on DNA from a genomic library and genomic sequences. RT-PCR was used to confirm that the genomic sequence can be transcribed into RNA. The extended 620 bp sequence, representing the full length of the expressed RNA gene sequence is shown in FIG. 7 and designated herein as SEQ ID NO:5. Shaded boxes in FIG. 7 indicate potential polyadenylation signals.

Rescue experiments using the cardiac myofibrillogenesis assay demonstrated that the full length MIR sequence was highly effective in promoting the rescue activity.

Example 15

Knockdown of Endogenous MIR RNA Using Double-stranded MIR Decreases Tropomyosin Expression and Disassembles Myofibrils In Normal Heart Cells Double-stranded RNA of the MIR gene (DS MIR) was introduced into normal beating heart cells by liposome-medicated transfection. Following transfection, after ten days in culture in Steinberg's solution, all of the normal hearts stopped beating. Confocal scanning microscopy revealed dramatically decreased tropomyosin expression level by antibody staining, and significant destruction of myofibril structures. By contrast, normal hearts incubated with DS MIR treated with a high concentration of RNaseONE (Promega, Madison, Wis.) exhibited normal beating and tropomyosin staining, and hence abolition of the inhibitory action of the double-stranded RNA. These results demonstrated that MIR is essential for myofibrillogenesis in normal hearts.

Example 16

Sequence Homology of MIR with a 5' Untranslated Region of axoSmN cDNA

In related studies, a full length cDNA encoding the axolotl homolog of the mammalian SmN, termed herein "axoSmN," was cloned. The mammalian SmN gene encodes a tissue-specific RNA slicing factor (Huntriss J D et al., 1993; Gerrelli D et al., 1994). Of note, comparison of the MIR cDNA sequence with the axoSmN sequence revealed an exact match of a portion of the MIR sequence (i.e., GCC GAT CCT TTG GAA TTT GTA CAT GTG ACC TCA AGG TTG CAC GCA TAT CCG AGC AGT TGC TGG ATT AGA GCA GGC ACT CCC TTG) (SEQ ID NO:6) with an identical sequence in the 5' untranslated region of the axoSmN gene. Referring to FIG. 7, the positions of these residues in the MIR cDNA sequence are indicated in italics. Referring to FIG. 8, a full-length cDNA sequence for axoSmN is shown. The underlined sequence in the 5'-untranslated region of axoSmN is the sequence exhibiting 100% sequence identity with a portion of the MIR cDNA. The shaded portion of the AxoSmN sequence represents a large deduced open reading frame showing homology to the mammalian SmN gene. Poly (A) tail and polyadenylation signal (in bold) are also indicated. The finding of the common sequence in MIR and axoSmN points to a potential relationship between MIR and the axoSmN gene, possibly through common interacting proteins.

Other Embodiments

While the above specification contains many specifics, these should not be construed as limitations on the scope of the invention, but rather as examples of preferred embodiments thereof. Many other variations are possible. Accordingly, the scope of the invention should be determined not by the embodiments illustrated, but by the appended claims and their legal equivalents.

LITERATURE CITED

Belaguli N S, Schildmeyer L A, Schwartz R J 1997 Organization and myogenic restricted expression of the murine serum response factor gene. A role for autoregulation. J Biol Chem. 1997 Jul. 18; 272(29):18222-31.

Brodsky L I et al. 1995 GeneBeeNET: Internet-based server for analyzing biopolymers structure. Biochemistry (Moscow), Vol. 60, No. 8, 1-8.

Chomczynski, P, Sacchi N. 1987. Single-step method of RNA isolation by acid guanidinium thiocyanate-phenol-chloroform extraction. Anal Biochem 163:156-159.

Davis L A, Lemanski L F 1987 Induction of myofibrillogenesis in cardiac lethal mutant axolotl hearts rescued by RNA derived from normal endoderm. Development 99:145-154.

Draghia-Akli R, Li X, Schwartz R J 1997 Enhanced growth by ectopic expression of growth hormone releasing hormone using an injectable myogenic vector. Nat Biotechnol. 1997 November; 15(12):1285-9.

Fransen M E, Lemanski L F 1988 Myocardial cell relationships during morphogenesis in normal and cardiac lethal mutant axolotls, *Ambystoma mexicanum*. Amer J Anat 183:245-257.

Humphrey R R 1968 A genetically determined absence of heart function in embryos of the Mexican axolotl (*Ambystoma mexicanum*). Anat Rec 162:475.

Ito S, Kamovsky M J 1968 Formaldehyde-glutaraldehyde fixatives containing trinitro compounds. J Cell Biol 112: 276-283.

Lemanski L F 1979 Role of tropomyosin in actin filament formation in embryonic salamander heart cells. J Cell Biol 82:227-238.

Lemanski L F, Paulson D J, Hill C S 1979 Normal anterior endoderm corrects the heart defect in cardiac mutant salamanders (*Ambystoma mexicanum*). Science 204:860-862.

Lemanski L F, LaFrance S M, Erginel-Unaltuna N, Luque E A, Ward S M, Fransen M E, Mangiacapra F J, Nakatsugawa M, Lemanski S L, Capone R B, Goggins K J, Nash B P, Bhatia R, Dube A, Gaur A, Zajdel R W, Zhu Y, Spinner B J, Pietras K M, Lemanski S F, Kovacs C P and Dube D K 1995 The Cardiac Mutant Gene c in Axolotls: Cellular, Developmental and Molecular Studies. Cell Molec Biol Res 41: 293-305

Lemanski, L F, Zajdel, R W, Nakatsugawa, M, Bhatia, R, Spinner, B J, Fransen, M E, Gaur, A F, McLean, M D, Lemanski, S L, and Dube, D K 1997 Molecular biology of heart development in the Mexican axolotl, *Ambystoma mexicanum*. J Tsitologiya (Cytology) 39: 918-927

Lemanski L F, Huang X, Zajdel R W, Lemanski S L, Zhang C, Meng F, Foster D, Li Q, Dube Smith S C, Armstrong J B 1990 Heart induction in wild-type and cardiac mutant axolotls (*Amybstoma mexicanum*). J Exp Zool 254:48-54.

Lemanski L F, Nakatsugawa M, Bhatia, R, Erginel-Unaltuna N, Spinner B J, and Dube D K 1996 A specific synthetic RNA promotes cardiac myofibrillogeneses in the Mexican axolotl. Biochem Biophys Res Commun 229:974-81.

Lemanski L F, Meng F, Lemanski S L, Dawson N, Zhang C, Li Q, Nagatsugawa M, Dube D K, Huang X 2001 Creation of chimeric mutant axolotls: a model to study early embryonic heart development in Mexican axolotls. Anat Embryol 203:335-342.

Pestova T V et al. 2001 Molecular mechanisms of translation initiation in eukaryotes. Proc Natl Acad Sci 98 (13):7029-7036.

Sanbe A, Gulick J, Hanks M C, Liang Q, Osinska H, Robbins J. Reengineering inducible cardiac-specific transgenesis with an attenuated myosin heavy chain promoter. Circ Res. 2003 Apr. 4;92(6):609-16.

Sepulveda J L, Vlahopoulos S, Iyer D, Belaguli N, Schwartz R J. Combinatorial expression of GATA4, Nkx2-5, and serum response factor directs early cardiac gene activity. J Biol Chem. 2002 Jul. 12; 277(28):25775-82.

Zackson S, Steinberg M 1986 Cranial neural crest cells exhibit directed migration on the pronephric duct pathway: further evidence for an in vivo adhesion gradient. Dev Biol 117:342-353.

Zajdel R W, McLean M D, Isitmangil G, Lemanski L F, Wieczorek D F, Dube D K 2000 Alteration of cardiac myofibrillogenesis by lioposme-mediated delivery of exogenous proteins and nucleic acids into whole embryonic hearts. Anat Embryol 201:217-228.

What is claimed is:

1. A purified nucleic acid comprising nucleotide sequence SEQ ID NOS: 1 or 5, wherein said sequences are capable of being transcribed into a myofibrillogenesis-inducing RNA (MIR) molecule.

2. The purified nucleic acid of claim 1, wherein said nucleotide sequence is transcribed into an RNA molecule having a secondary structure that permits specific binding to at least one MIR-binding protein.

3. A purified myofibrillogenesis-inducing RNA (MIR) molecule comprising a ribonucleic acid sequence which is fully complementary over the full length of SEQ ID NO: 5 and induces myofibrillogenesis in living cells.

4. A vector comprising a purified nucleic acid cDNA of SEQ ID NO: 5 that is transcribed into a myofibrillogenesis-inducing RNA (MIR) molecule.

5. The vector of claim 4, wherein the purified nucleic acid further encodes a MIR-binding protein.

* * * * *

```
                       SEQUENCE LISTING

<160> NUMBER OF SEQ ID NOS: 8

<210> SEQ ID NO 1
<211> LENGTH: 166
<212> TYPE: DNA
<213> ORGANISM: Ambystoma mexicanum

<400> SEQUENCE: 1
agcaccactc catttttgga acacctcctc taccgtggat gagaggcgga gccgatcctt      60
tggaatttgt acatgtgacc tcaaggttgc acgcatatcc gagcagttgc tggattagag     120
caggcactcc cttatcggct ttggaatgga gaccagaaag aacact                    166

<210> SEQ ID NO 2
<211> LENGTH: 22
<212> TYPE: DNA
```

```
<213> ORGANISM: Ambystoma mexicanum

<400> SEQUENCE: 2
gtgttctttc tgggctccat tc                                              22

<210> SEQ ID NO 3
<211> LENGTH: 24
<212> TYPE: DNA
<213> ORGANISM: Ambystoma mexicanum

<400> SEQUENCE: 3
agcaccactc cattttgga acac                                             24

<210> SEQ ID NO 4
<211> LENGTH: 166
<212> TYPE: DNA
<213> ORGANISM: Ambystoma mexicanum

<400> SEQUENCE: 4
agcaccactc cattttgga acacctcctc taccgtggat gagaggcgga gccgatcctt      60
tggaatttgt acatgtgacc tcaaggttgc actcatatcc gagcagttgc tggattagag    120
caggcactcc cttatcggct tggaatgga gaccagaaag aacact                    166

<210> SEQ ID NO 5
<211> LENGTH: 620
<212> TYPE: DNA
<213> ORGANISM: Ambystoma mexicanum

<400> SEQUENCE: 5
gttcaaaaat aacattttaa ttttgtatct cctaatacag ccatcataac atattctagg     60
actggtataa ctgtatagac aaactccctt cctaggatat tttgggaaag tgctggatag    120
ccggggagaa cagcaccttt ctctcaggca atgttaaata ggtgcaatgt tttcacatgt    180
tatggaatat atcttccaac tgactgacca agagaaaaca atgaaccaca ataccggaaa    240
cttcattcgt ttgacccttc cacccactcg agcgtcaaca tgcccaggcc gctacccctt    300
gacacacgtg tagcaccact ccattttgg aacacctcct ctaccgtgga tgagaggcgg    360
agccgatcct ttggaatttg tacatgtgac ctcaaggttg cacgcatatc cgagcagttg    420
ctggattaga gcaggcactc ccttatcggc tttggaatgg agaccagaaa gaacaatgtg    480
ggacagctga tatggagggc agggcgggga agtgagagaa agggcaacaa tagagggcag    540
ataagggggg gagggcaagg aataaacagg aactgcagtg ggagaaaacg tcgaacgaga    600
aaaaaaaaaa aaaaaaaaa                                                 620

<210> SEQ ID NO 6
<211> LENGTH: 85
<212> TYPE: DNA
<213> ORGANISM: Ambystoma mexicanum

<400> SEQUENCE: 6
agccgatcct ttggaatttg tacatgtgac ctcaaggttg cacgcatatc cgagcagttg     60
ctggattaga gcaggcactc ccttg                                           85

<210> SEQ ID NO 7
<211> LENGTH: 985
<212> TYPE: DNA
<213> ORGANISM: Ambystoma mexicanum

<400> SEQUENCE: 7
```

-continued

```
agccgatcct tggaatttg tacatgtgac ctcaaggttg cacgcatatc cgagcagttg      60
ctggattaga gcaggcactc ccttgctcca acacgttgac tttaggatgc gctgtatcct    120
gcaagatggc cgcatcttta ttggtacttt caaagctttc gataaacaca tgaatctgat    180
tctctgtgac tgcgacgagt tcaggaagat aaaacctaag aattctaaac agccagagcg    240
tgaagagaag agggtccttg gctggtact actccgtggc gaaaaccttg tatctatgac     300
cgtggaagga ccaccccaa aagatactgg tattgcccgt gtcccactgg caggagctgc    360
aggaggacct ggtgttggaa gggctgcagg gagaggagtg ccagcaggtg taccaatacc    420
gcaagcacca gcgggcttgg caggcccagt gcgaggtgtt ggtggcccat cccagcaggt    480
gatgacacca cagggacgtg gaaatccatc tggtgctagc attgcaggag caccaacgca    540
gtaccagcct ggtgggagag gtggcccgat gctgccaatg ggctgtggtg gacctccagg    600
catgatggga ccacccccgg gcatgaggcc acctatgggc ccacctatgg gaatgccccc    660
aggccgaggt ggttcaatgg gcatgcctcc acctggtatg cgacctccac cacctggtat    720
gagaggcgac cgattctaga aacaaaggtt cacctcgtgg gaagcgttcc tcaagaccat    780
aaatcgatta cttgtttgtg gattgaaagt tgatggatgt gttgagtgga tgcccagtgc    840
acttactggc agttggaagc ccttgatagt agctactttt actttcagga gatctggctg    900
aagctgttca ttttcttat ttacatgtaa atgtttttaa taaacttcta aaatggcaaa    960
aaaaaaaaaa aaaaaaaaa aaaaa                                          985
```

<210> SEQ ID NO 8
<211> LENGTH: 210
<212> TYPE: PRT
<213> ORGANISM: Ambystoma mexicanum
<400> SEQUENCE: 8

```
Met Arg Cys Ile Leu Gln Asp Gly Arg Ile Phe Ile Gly Thr Phe Lys
 1               5                  10                  15

Ala Phe Asp Lys His Met Asn Leu Ile Leu Cys Asp Cys Asp Glu Phe
            20                  25                  30

Arg Lys Ile Lys Pro Lys Asn Ser Lys Gln Pro Glu Arg Glu Glu Lys
        35                  40                  45

Arg Val Leu Gly Leu Val Leu Leu Arg Gly Glu Asn Leu Val Ser Met
    50                  55                  60

Thr Val Glu Gly Pro Pro Lys Asp Thr Gly Ile Ala Arg Val Pro
65                  70                  75                  80

Leu Ala Gly Ala Ala Gly Gly Pro Gly Val Gly Arg Ala Ala Gly Arg
                85                  90                  95

Gly Val Pro Ala Gly Val Pro Ile Pro Gln Ala Pro Ala Gly Leu Ala
            100                 105                 110

Gly Pro Val Arg Gly Val Gly Gly Pro Ser Gln Val Met Thr Pro
        115                 120                 125

Gln Gly Arg Gly Asn Pro Ser Gly Ala Ser Ile Ala Gly Ala Pro Thr
    130                 135                 140

Gln Tyr Gln Pro Gly Gly Arg Gly Gly Pro Met Leu Pro Met Gly Cys
145                 150                 155                 160

Gly Gly Pro Pro Gly Met Met Gly Pro Pro Gly Met Arg Pro Pro
                165                 170                 175

Met Gly Pro Pro Met Gly Met Pro Pro Gly Arg Gly Gly Ser Met Gly
            180                 185                 190
```

```
-continued

Met Pro Pro Pro Gly Met Arg Pro Pro Pro Gly Met Arg Gly Asp
        195                 200                 205

Arg Phe
    210
```